United States Patent
Nakahata et al.

(10) Patent No.: US 10,669,529 B2
(45) Date of Patent: Jun. 2, 2020

(54) METHOD FOR INDUCING VASCULAR ENDOTHELIAL CELLS

(71) Applicants: Kyoto University, Kyoto (JP); Osaka University, Osaka (JP)

(72) Inventors: Tatsutoshi Nakahata, Kyoto (JP); Megumu Saito, Kyoto (JP); Akira Niwa, Kyoto (JP); Ryo Ota, Kyoto (JP); Kiyotoshi Sekiguchi, Osaka (JP)

(73) Assignees: Kyoto University, Kyoto (JP); Osaka University, Osaka (JP)

(*) Notice: Subject to any disclaimer, the term of this patent is extended or adjusted under 35 U.S.C. 154(b) by 32 days.

(21) Appl. No.: 15/745,425

(22) PCT Filed: Jul. 14, 2016

(86) PCT No.: PCT/JP2016/070908
§ 371 (c)(1),
(2) Date: Jan. 16, 2018

(87) PCT Pub. No.: WO2017/014165
PCT Pub. Date: Jan. 26, 2017

(65) Prior Publication Data
US 2018/0208893 A1    Jul. 26, 2018

(30) Foreign Application Priority Data
Jul. 17, 2015 (JP) ................................ 2015-142732

(51) Int. Cl.
| | |
|---|---|
| *C12N 5/10* | (2006.01) |
| *C12N 15/09* | (2006.01) |
| *A61K 35/44* | (2015.01) |
| *C12N 5/071* | (2010.01) |
| *C07K 14/78* | (2006.01) |
| *A61L 27/00* | (2006.01) |

(52) U.S. Cl.
CPC .............. *C12N 5/069* (2013.01); *A61K 35/44* (2013.01); *A61L 27/00* (2013.01); *C07K 14/78* (2013.01); *C12N 5/10* (2013.01); *C12N 15/09* (2013.01); *C12N 2501/155* (2013.01); *C12N 2501/165* (2013.01); *C12N 2533/52* (2013.01)

(58) Field of Classification Search
CPC .......... C12N 5/069; C12N 5/10; C12N 15/09; A61L 27/00; A61K 35/44
See application file for complete search history.

(56) References Cited

U.S. PATENT DOCUMENTS

| | | | |
|---|---|---|---|
| 5,843,780 A | 12/1998 | Thomson | |
| 2009/0068742 A1 | 3/2009 | Yamanaka | |
| 2014/0045265 A1* | 2/2014 | Belmonte | ............ C12N 5/0647 435/377 |
| 2015/0017724 A1 | 1/2015 | Gerecht et al. | |
| 2016/0052994 A1 | 2/2016 | Sekiguchi et al. | |
| 2017/0114322 A1* | 4/2017 | Hasegawa | ............ C12N 5/0606 |
| 2018/0171291 A1 | 6/2018 | Gerecht et al. | |

FOREIGN PATENT DOCUMENTS

| | | | |
|---|---|---|---|
| WO | WO 02/048349 | 6/2002 | |
| WO | WO 07/069666 | 6/2007 | |
| WO | WO 11/115308 | 9/2011 | |
| WO | WO 12/006440 | 1/2012 | |
| WO | WO 14/103534 | 7/2014 | |
| WO | WO-2015147047 A1 * | 10/2015 | ........... C12N 5/0606 |

OTHER PUBLICATIONS

Assmus et al., Dec. 10, 2002, Transplantation of progenitor cells and regeneration enhancement in acute myocardial infarction (TOPCARE-AMI), Circulation, 106:3009-3017.
Choi et al., Mar. 2009, Hematopoietic and endothelial differentiation of human induced pluripotent stem cells, Stem Cells, 27(3):559-567.
Descamps et al., 2012, Vascular differentiation from embryonic stem cells: novel technologies and therapeutic promises, Vascul. Pharmacol., 56(5-6):267-279.
Dzau et al., Jul. 2005, Therapeutic potential of endothelial progenitor cells in cardiovascular diseases, Hypertension, 46:7-18.
Miyazaki et al., 2012, Laminin E8 fragments support efficient adhesion and expansion of dissociated human pluripotent stem cells, Nat. Commun., 3:1236 (abstract).
Niwa et al., 2011, A novel serum-free monolayer culture for orderly hematopoietic differentiation of human pluripotent cells via mesodermal progenitors, PLoS One, 6(7):e22261.
Prasain et al., Nov. 2014, Differentiation of human pluripotent stem cells to cells similar to cord-blood endothelial colony-forming cells, Nature Biotechnology, 32(11):1151-1160.
Schnaper et al., 1993, Role of laminin in endothelial cell recognition and differentiation, Kidney Int., 43(1):20-25.
Yanagimachi et al., 2013, Robust and highly-efficient differentiation of functional monocytic cells from human pluripotent stem cells under serum- and feeder cell-free conditions, PLoS One, 8(4):e49243.
Yousif et al., Jan./Feb. 2013, Laminin isoforms in endothelial and perivascular basement membranes, Cell Adhesion & Migration, 7(1):101-110.
International Search Report dated Sep. 27, 2016 in patent application No. PCT/JP2016/070908.
(Continued)

*Primary Examiner* — Ruth A Davis
(74) *Attorney, Agent, or Firm* — Knobbe, Martens, Olsen & Bear, LLP

(57) ABSTRACT

Provided is a method for producing vascular endothelial cells from pluripotent stem cells, the method comprising the following steps (i) to (iii): (i) a step of culturing pluripotent stem cells in a culture medium comprising a BMP, on a culture vessel coated with a first matrix, to produce mesodermal progenitor cells; (ii) a step of dissociating the resulting cells into single cells; and (iii) a step of culturing the resulting cells in a culture medium comprising VEGF, on a culture vessel coated with a second matrix selected from the group consisting of laminin-411 or a fragment thereof, laminin-511 or a fragment thereof, Matrigel, type IV collagen and fibronectin.

10 Claims, 7 Drawing Sheets

Specification includes a Sequence Listing.

(56) References Cited

OTHER PUBLICATIONS

Rodin, S. et al. 2010 "Long-term self-renewal of human pluripotent stem cells on human recombinant laminin-511" Nature Biotechnology 28: 611-617 (in 7 pages).
Supplementary European Search Report in corresponding European Application No. EP 16827725.9, dated Jan. 17, 2019.
Blancas A.A. et al. 2011 "Endothelial cells from embryonic stem cells in a chemically defined medium" Stem Cells and Development 20(12): 2153-2161.
Rodin, S. et al. 2010 "Long-term self-renewal of human pluripotent stem cells on human redombinant laminin-511" Nature Biotechnology 28: 611 (in 7 pages).
Supplementary European Search Report in corresponding European Application No. EP 16 82 7725, dated Jan. 17, 2019.
Qu, H. et al. 2014 "Laminin 411 acts as a potent inducer of umbilical cord mesenchymal stem cell differentiation into insulin-producing cells" J Translational Medicine 12: 135 (in 12 pages).
Miyazaki et al., 2012, Laminin E8 fragments support efficient adhesion and expansion of dissociated human pluripotent stem cells, Nat. Commun., 3:1236.
Prasain et al., Nov. 2014, Differentiation of human pluripotent stem cells to cells similar to cord-blood endothelial colony-forming cells, Nature Biotechnology, 32(11):1151-1157.
Yanagimachi et al., 2013, Robust and highly-efficient differentiation of functional monocytic cells from human pluripotent stem cells under serum- and feeder cell-free conditions, PLoS One, 8(4):e59243.

* cited by examiner

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: L803-mts
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (11)..(11)
<223> OTHER INFORMATION: PHOSPHORYLATION

<400> SEQUENCE: 1

Gly Lys Glu Ala Pro Pro Ala Pro Pro Gln Ser Pro
1               5                   10

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
gaggtctata taagcagagc tctctggcta acta                              34

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
cattggcttc atcatgatga tgatgatgat gaagc                             35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
catcatgatg aagccaatga aacagcagaa tttgc                             35
```

```
<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
gcagaattct caatgagagt ttcttggagt attcc                              35
```

METHOD FOR INDUCING VASCULAR ENDOTHELIAL CELLS

CROSS REFERENCE TO RELATED APPLICATIONS

This application is a U.S. national application under 35 U.S.C. § 371 of International Application No.: PCT/JP2016/070908, filed Jul. 14, 2016, which claims priority under 35 U.S.C. § 365 to Japanese Patent Application No. 2015-142732, filed Jul. 17, 2015.

Reference to Sequence Listing

A Sequence Listing is submitted herewith submitted as an ASCII text file via EFS-Web and is hereby incorporated by reference in accordance with 37 C.F.R. § 1.52(e). The name of the ASCII text file for the Sequence Listing is SeqList-TOYA230-001APC.txt, the date of creation of the ASCII text file is Jul. 14, 2016, and the size of the ASCII text file is 2 KB.

TECHNICAL FIELD

The present invention relates to a method for producing vascular endothelial cells from pluripotent stem cells.

BACKGROUND ART

Mammalian blood vessels are composed of three layers: the adventitia, media and intima, and the intima is covered with a layer of vascular endothelial cells. The vascular endothelial cells release various types of vasoactive substances to control the contraction and expansion of blood vessels, and also protect blood vessels by preventing the adhesion and aggregation of platelets.

Examples of diseases in which vascular endothelial cells are involved include arteriosclerosis that begins with a decrease in the function of endothelial cells present in vascular intima. Endothelial dysfunction, namely, the loss of endothelial function, induces vascular diseases, such as for example, atherosclerosis. Vascular endothelial cells and endothelial progenitor cells (EPCs) have been suggested to be useful for therapeutic applications, and cases have been reported in which a revascularization therapy of transplanting autologous EPCs to patients with severe ischemic diseases including coronary artery diseases and lower limb ischemic diseases (such as Buerger's disease, obstructive arteriosclerosis, etc.) was performed to obtain favorable results (Non-patent Documents 1 and 2). The above described effect of improving ischemia has been confirmed to be dependent on the number of EPCs administered, and thus it is important to obtain and administer a larger amount of EPCs. However, the number and the function of EPCs obtained from autologous blood or bone marrow fluid of the patients are often decreased, and in such cases, a sufficient therapeutic effect cannot be obtained.

On the other hand, cells with pluripotency have hitherto been reported, such as induced pluripotent stem cells (iPS cells) which can be obtained by introducing undifferentiated cell-specific genes into embryonic stem cells (ES cells) or somatic cells (Patent Documents 1 and 2). These cells are drawing attention as useful materials, since they can be grown indefinitely, and there is a possibility that vascular endothelial cells for use in transplantation therapy can be obtained by applying a differential stimulus to these cells.

So far, a method for inducing the differentiation of human embryonic stem cells into endothelial cells (Patent Document 3), and methods for inducing the differentiation of human pluripotent stem cells into mesodermal cells have been examined (Patent Document 4, Non-patent Document 3 and Non-patent Document 4). However, no method has been reported to date which allows the induction to highly functional vascular endothelial cells from pluripotent stem cells at a high efficiency.

PRIOR ART DOCUMENTS

Patent Documents

Patent Document 1: U.S. Pat. No. 5,843,780
Patent Document 2: WO 2007/069666
Patent Document 3: WO 2012/006440
Patent Document 4: WO 2011/115308

Non-Patent Documents

Non-patent Document 1: Assmus B, et al, Circulation. 106: pp. 3009 to 3017, 2002
Non-patent Document 2: Dzau et al., Hypertension. 46: pp. 7 to 18, 2005
Non-patent Document 3: Niwa A, et al, PLoS One. 6: e22261 2011
Non-patent Document 4: Yanagimachi M D, et al, PLoS One. 8: e59243, 2013

SUMMARY OF THE INVENTION

Problems to be Solved by the Invention

The present invention aims to efficiently produce vascular endothelial cells from pluripotent stem cells. Accordingly, an object of the present invention is to provide a method for efficiently inducing the differentiation of human pluripotent stem cells, particularly, human induced pluripotent stem cells, into vascular endothelial cells.

Means for Solving the Problems

As a result of attempts to solve the above-described problem, the present inventors have found out that, by varying as appropriate matrices for coating culture vessels to be used in the steps of inducing pluripotent stem cells into mesodermal progenitor cells, and then further into endothelial cells, it is possible to induce the differentiation into vascular endothelial cells at a high purity. Further, by using the above described method, the inventors have succeeded in producing highly functional vascular endothelial cells, without being affected by individual preference of each cell line of pluripotent stem cells to differentiate into endothelial cells, thereby completed the present invention.

In other words, the present invention is as follows.
[1] A method for producing vascular endothelial cells from pluripotent stem cells, the method including the following steps (i) to (iii):
  (i) a step of culturing pluripotent stem cells in a culture medium containing a BMP (Bone Morphogenetic Protein), on a culture vessel coated with a first matrix, to produce mesodermal progenitor cells;
  (ii) a step of dissociating the mesodermal progenitor cells obtained in the step (i) into single cells; and
  (iii) a step of culturing the cells obtained in the step (ii) in a culture medium containing VEGF (Vascular Endothelial Growth Factor), on a culture vessel coated with a second matrix selected from the group consisting of laminin-411 (LM411) or a fragment thereof, laminin-511 (LM511) or a fragment thereof, Matrigel (registered trademark), type IV collagen and fibronectin.

[2] The method according to [1], wherein the second matrix used in the step (iii) is a fragment of laminin-411.

[3] The method according to [1] or [2], wherein the fragment of laminin-411 is laminin-411 E8.

[4] The method according to any one of [1] to [3], wherein the first matrix used in the step (i) is Matrigel, or laminin-511 or a fragment thereof.

[5] The method according to [4], wherein the fragment of laminin-511 is laminin-511 E8.

[6] The method according to any one of [1] to [5], wherein the BMP is BMP4.

[7] The method according to any one of [1] to [6], wherein the culture medium used in the step (i) further comprises a GSK (Glycogen Synthase Kinase) 3β inhibitor and VEGF.

[8] The method according to [7], wherein the GSK3β inhibitor is CHIR99021.

[9] The method according to any one of [1] to [8], wherein the step (i) is carried out for two days or three days.

[10] The method according to any one of claims [1] to [9], wherein the step (iii) is carried out for four days.

[11] A method for producing vascular endothelial cells from mesodermal progenitor cells, the method including:
a step of culturing mesodermal progenitor cells in a culture medium containing VEGF, on a culture vessel coated with a matrix selected from the group consisting of laminin-411 or a fragment thereof, laminin-511 or a fragment thereof, Matrigel, type IV collagen and fibronectin.

[12] The method according to [11], wherein the matrix is a fragment of laminin-411.

[13] The method according to [12], wherein the fragment of laminin-411 is laminin-411 E8.

[14] The method according to any one of [11] to [13], wherein the step is carried out for four days.

[15] A vascular endothelial cell obtained by the method according to any one of [1] to [14].

[16] A revascularizing agent including the vascular endothelial cell according to [15].

[17] A kit for producing vascular endothelial cells, the kit including a fragment of laminin-411.

[18] The kit according to [17], wherein the fragment of laminin-411 is laminin-411 E8.

Effect of the Invention

According to the present invention, it is possible to efficiently obtain vascular endothelial cells for use in transplantation therapy and the like for treating patients with ischemic diseases including coronary artery diseases and lower limb ischemic diseases (such as Buerger's disease, obstructive arteriosclerosis, etc.).

BRIEF DESCRIPTION OF THE DRAWINGS

In FIG. 4, the number indicates the content in percentage of KDR-positive mesodermal progenitor cells.

EMBODIMENTS FOR CARRYING OUT THE INVENTION

Figure 1:
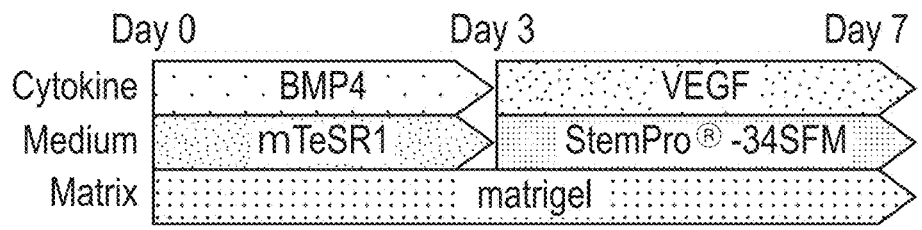
FIG. 1 shows a scheme for inducing the differentiation into vascular endothelial cells according to a conventional method.

The present invention will now be described in detail.

The present invention provides:

a method for producing vascular endothelial cells from pluripotent stem cells, the method including the following steps (i) to (iii):

(i) a step of culturing pluripotent stem cells in a culture medium comprising a BMP, on a culture vessel coated with a first matrix, to produce mesodermal progenitor cells;

(ii) a step of dissociating the mesodermal progenitor cells obtained in the step (i) into single cells; and (iii) a step of culturing the cells obtained in the step (ii) in a culture medium comprising VEGF, on a culture vessel coated with a second matrix selected from the group consisting of laminin-411 or a fragment thereof, laminin-511 or a fragment thereof, Matrigel, type IV collagen and fibronectin.

Since the above described step (i) is a step of producing mesodermal progenitor cells from pluripotent stem cells, the present invention also provides a method for producing mesodermal progenitor cells from pluripotent stem cells. Likewise, since the above described step (iii) is a step of producing vascular endothelial cells from mesodermal progenitor cells, the present invention also provides a method for producing vascular endothelial cells from mesodermal progenitor cells.

<Pluripotent Stem Cells>

Pluripotent stem cells which can be used in the present invention are stem cells having pluripotency, which is an ability to differentiate into all types of cells present in a living body, as well as having proliferative capacity. Examples thereof include, but are not particularly limited to, embryonic stem (ES) cells; embryonic stem (ntES) cells derived from a cloned embryo obtained by nuclear transfer, Germline stem cells ("GS cells"); embryonic germ cells ("EG cell"); induced pluripotent stem (iPS) cells; and pluripotent cells (Muse cells) derived from cultured fibroblasts and bone marrow stem cells. Preferred pluripotent stem cells are ES cells, ntES cells and iPS cells.

(A) Embryonic Stem Cells

ES cells are stem cells which are established from the inner cell mass of an early embryo (such as a blastocyst) of a mammal, such as a human or a mouse, and which have pluripotency and proliferative capacity by self-renewal.

ES cells are embryo-derived stem cells originated from the inner cell mass of a blastocyst, which is an embryo formed following the eight-cell stage and the morula-stage of a fertilized egg. ES cells have an ability to differentiate into all the cells constituting an adult body, so-called pluripotency, and proliferative capacity by self-renewal. ES cells were discovered in mice in 1981 (M. J. Evans and M. H. Kaufman (1981), Nature 292: pp. 154 to 156). Subsequently, ES cell lines were established also in primates, including humans, monkeys, and the like (J. A. Thomson et al. (1998), Science 282: pp. 1145 to 1147; J. A. Thomson et al. (1995), Proc. Natl. Acad. Sci. USA, 92: pp. 7844 to 7848; J. A. Thomson et al. (1996), Biol. Reprod., 55: pp. 254 to 259; J. A. Thomson and V. S. Marshall (1998), Curr. Top. Dev. Biol., 38: pp. 133 to 165).

ES cells can be established by recovering the inner cell mass from a blastocyst of a fertilized egg of a subject animal, and culturing the inner cell mass on fibroblast feeder cells. Further, the cells can be maintained by subculturing using a culture medium supplemented with a substance(s) such as leukemia inhibitory factor (LIF) and/or basic fibroblast growth factor (bFGF). Methods for establishing and maintaining human and monkey ES cells are disclosed, for example, in: U.S. Pat. No. 5,843,780; Thomson J A, et al. (1995), Proc Natl. Acad. Sci. USA. 92: pp. 7844 to 7848; Thomson J A, et al. (1998), Science. 282: pp. 1145 to 1147; H. Suemori et al. (2006), Biochem. Biophys. Res. Commun., 345: pp. 926 to 932; M. Ueno et al. (2006), Proc. Natl. Acad. Sci. USA, 103: pp. 9554 to 9559; H. Suemori et al. (2001), Dev. Dyn., 222: pp. 273 to 279; H. Kawasaki et al. (2002), Proc. Natl. Acad. Sci. USA, 99: pp. 1580 to 1585; Klimanskaya I, et al. (2006), Nature. 444: pp. 481 to 485, and the like.

For example, DMEM/F-12 medium supplemented with 0.1 mM 2-mercaptoethanol, 0.1 mM non-essential amino acid, 2 mM L-glutamic acid, 20% KSR and 4 ng/ml bFGF can be used as a culture medium for preparing ES cells, and human ES cells can be maintained at 37° C. under a moist atmosphere of 2% $CO_2$ and 98% air (O. Fumitaka et al. (2008), Nat. Biotechnol., 26: pp. 215 to 224). Further, ES cells need to be subcultured every three to four days, and the subculture can be carried out using, for example, 0.25% trypsin and 0.1 mg/ml collagenase IV in PBS containing 1 mM $CaCl_2$ and 20% KSR.

The selection of ES cells can be generally carried out by the Real-Time PCR method, using as an index/indices the expression of a gene marker(s) such as alkaline phosphatase, Oct-3/4 and/or Nanog. In the selection of human ES cells, in particular, the expression of a gene marker(s) such as OCT-3/4, NANOG and/or ECAD can be used as an index/indices (E. Kroon et al. (2008), Nat. Biotechnol., 26: pp. 443 to 452).

Human ES cell lines, such as, for example, WA01 (H1) and WA09 (H9) can be obtained from WiCell Research Institute; and KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis and cells which serve as the origin for spermatogenesis. Germline stem cells can be induced to differentiate into cells of various lineages, in the same manner as ES cells, and have properties capable of creating, for example, a chimeric mouse, when transplanted into a mouse blastocyst (M. Kanatsu-Shinohara et al. (2003) Biol. Reprod., 69: pp. 612 to 616; and K. Shinohara et al. (2004), Cell, 119: pp. 1001 to 1012). Germline stem cells are capable of renewing themselves in a culture medium containing a glial cell line-derived neurotrophic factor (GDNF)), and are obtainable by repeated subculture under the same culture conditions as those for ES cells (Masanori Takebayashi et al., (2008), Experimental Medicine, Vol. 26, Issue 5 (special number), pp. 41 to 46, YODOSHA (Tokyo, Japan)).

(C) Embryonic Germ Cells

Embryonic germ cells are cells which are established from primordial germ cells in the prenatal period, and which have pluripotency similar to that of ES cells. Embryonic germ cells can be established by culturing primordial germ cells in the presence of a substance(s) such as LIF, bFGF and/or a stem cell factor (Y. Matsui et al. (1992), Cell, 70: pp. 841 to 847; and J. L. Resnick et al. (1992), Nature, 359: pp. 550 to 551).

(D) Induced Pluripotent Stem Cells

Induced pluripotent stem (iPS) cells are artificial stem cells which are derived from somatic cells, and which have properties almost equivalent to those of ES cells, for example, pluripotency and proliferative capacity by self-renewal. Induced pluripotent stem cells can be prepared by introducing specific reprogramming factors in the form of DNA or protein into somatic cells (K. Takahashi and S. Yamanaka (2006) Cell, 126: pp. 663 to 676; K. Takahashi et al. (2007), Cell, 131: pp. 861 to 872; J. Yu et al. (2007), Science, 318: pp. 1917 to 1920; Nakagawa, M. et al., Nat. Biotechnol. 26: pp. 101 to 106 (2008); and WO 2007/069666). The reprogramming factor may be a gene specifically expressed in ES cells, a gene which plays an important role in maintaining the undifferentiated state of ES cells, or a gene product thereof. Examples of combinations of genes which function as reprogramming factors include, but are not particularly limited to: OCT3/4, SOX2 and KLF4; OCT3/4, KLF4 and C-MYC; OCT3/4, SOX2, KLF4 and C-MYC; OCT3/4 and SOX2; OCT3/4, SOX2 and NANOG; OCT3/4, SOX2 and LIN28; OCT3/4 and KLF4; and the like.

These factors can be introduced into somatic cells in the form of protein, for example, by a method such as lipofection, fusion with a cell membrane permeable peptide or microinjection. Alternatively, they can be introduced into somatic cells in the form of DNA, for example, by a method such as the use of a vector, for example, a virus, a plasmid or an artificial chromosome; lipofection; the use of liposome; or microinjection. Examples of the virus vector include retrovirus vectors, lentivirus vectors (both are described in Cell, 126, pp. 663 to 676, 2006; Cell, 131, pp. 861 to 872, 2007; and Science, 318, pp. 1917 to 1920, 2007), adenovirus vectors (Science, 322, pp. 945 to 949, 2008), adeno-associated virus vectors and Sendai virus vectors. Examples of the artificial chromosome vector include human artificial chromosome (HAC) vectors, yeast artificial chromosome (YAC) vectors and bacterial artificial chromosome (BAC, PAC) vectors. Examples of the plasmid which may be used include plasmids for use in mammalian cells (Science, 322: pp. 949 to 953, 2008). The vector may contain a regulatory sequence(s) such as a promoter, an enhancer, a ribosome binding sequence, a terminator and/or a polyadenylation site so as to enable the expression of nuclear reprogramming factors. If necessary, the vector may also contain a sequence of a selectable marker such as a drug resistance gene (for example, kanamycin resistance gene, ampicillin resistance gene, or puromycin resistance gene), a thymidine kinase gene, or a diphtheria toxin gene; or a sequence of a reporter gene such as green fluorescent protein (GFP), β-glucuronidase (GUS) or FLAG. Further, in order to delete, after the introduction of the above vector into somatic cells, the genes encoding the reprogramming factors, or both the promoters and the genes encoding the reprogramming factors linked thereto, the vector may include LoxP sequences upstream and downstream of these sequences.

In order to enhance the induction efficiency in the reprogramming process, it is also possible to use any of the followings, for example, in addition to the above described factors: histone deacetylase (HDAC) inhibitors [for example, low molecular weight inhibitors such as valproic acid (VPA) (Nat. Biotechnol., 26 (7): pp. 795 to 797 (2008)), trichostatin A, sodium butyrate, MC 1293 and M344; and nucleic acid expression inhibitors such as siRNAs and shRNAs against HDAC (e.g., HDAC1 siRNA Smartpool (registered trademark; Millipore), HuSH 29mer shRNA Constructs against HDAC1 (OriGene)) and the like]; DNA methyltransferase inhibitors (such as 5'-azacytidine) (Nat. Biotechnol., 26 (7): pp. 795 to 797 (2008)); G9a histone methyltransferase inhibitors [for example, low molecular weight inhibitors such as BIX-01294 (Cell Stem Cell, 2: pp. 525 to 528 (2008)); and nucleic acid expression inhibitors such as siRNAs and shRNAs against G9a (e.g., G9a siRNA (human) (Santa Cruz Biotechnology)) and the like]; L-channel calcium agonists (such as Bayk8644) (Cell Stem Cell, 3, pp. 568 to 574 (2008)); p53 inhibitors (such as siRNAs and shRNAs against p53 (Cell Stem Cell, 3, pp. 475 to 479 (2008)); UTF1 (Cell Stem Cell, 3, pp. 475 to 479 (2008)); Wnt Signaling (such as soluble Wnt3a) (Cell Stem Cell, 3, pp. 132 to 135 (2008)); 2i/LIF (2i is an inhibitor of mitogen-activated protein kinase signaling and glycogen synthase kinase-3, PloS Biology, 6 (10), pp. 2237 to 2247 (2008)); miRNAs such as miR-291-3p, miR-294 and miR-295 (R. L. Judson et al., Nat. Biotech., 27: pp. 459 to 461) (2009); and the like.

Examples of the culture medium to be used for inducing iPS cells include: (1) DMEM, DMEM/F12 and DME media containing from 10 to 15% FBS (these media can further contain any of LIF, penicillin/streptomycin, puromycin, L-glutamine, non-essential amino acids, β-mercaptoethanol and the like, as appropriate); and (2) ES cell culture media containing bFGF or SCF (Stem Cell Factor), such as media for culturing mouse ES cells (e.g. TX-WES medium; Thromb-X) and media for culturing primate ES cells (e.g. media for culturing primate (human and monkey) ES cells; ReproCELL, Kyoto, Japan).

Culture of the cells can be carried out, for example, by a culture method in which: somatic cells and reprogramming factors (DNA or protein) are brought into contact on DMEM or DMEM/F12 medium containing 10% FBS at 37° C. in the presence of 5% $CO_2$, followed by culturing for about 4 to 7 days; the cells are then seeded again on feeder cells (such as mitomycin C-treated STO cells or SNL cells); and cultured in a bFGF-containing medium for culturing primate ES cells from about Day 10 after the contact between the somatic cells and the reprogramming factors, thereby allowing iPS-like colonies to form after about 30 to about 45 days, or later, after the contact.

Alternatively, the cells can be cultured on feeder cells (such as mitomycin C-treated STO cell or SNL cell) using a 10% FBS-containing DMEM medium (the medium can further contain any of LIF, penicillin/streptomycin, puromycin, L-glutamine, non-essential amino acids, β-mercaptoethanol and the like, as appropriate) at 37° C. in the presence of 5% $CO_2$, thereby allowing ES-like colonies to form after about 25 to about 30 days, or later, after the contact. Examples of preferred methods include: a method in which somatic cells themselves to be reprogrammed are used instead of the feeder cells (Takahashi K, et al. (2009), PLoS One. 4: e8067 or WO2010/137746); and a method in which an extracellular matrix (such as Laminin-5 (WO2009/123349) or Matrigel (BD Biosciences)) is used instead.

Other examples of the culture method include a method in which a serum-free medium is used in the culture (Sun N, et al. (2009), Proc Natl Acad Sci USA. 106: pp. 15720 to 15725). Further, iPS cells may be established under hypoxic conditions (at an oxygen concentration of not less than 0.1% and not more than 15%) in order to improve the establishment efficiency (Yoshida Y, et al. (2009), Cell Stem Cell. 5: pp. 237 to 241 or WO2010/013845).

During the above described culture, the culture medium is replaced with fresh medium once every day, from Day 2 onwards after the start of the culture. Further, the number of somatic cells to be used in the nuclear reprogramming is within the range of from about $5 \times 10^3$ to about $5 \times 10^6$ cells per 100 cm$^2$ of a culture dish, but not particularly limited thereto.

iPS cells can be selected based on the shape of each formed colony. In cases where a drug resistance gene, which is expressed in conjunction with a gene to be expressed upon reprogramming of a somatic cell (such as Oct3/4 or Nanog), was introduced as a marker gene, established iPS cells can be selected by culturing the cells using a culture medium containing the corresponding drug (selective culture medium). Further, iPS cells can be selected: by observation under a fluorescence microscope in the case of using a fluorescent protein gene as a marker gene; by addition of a luminescent substrate in the case of using a luminescent enzyme gene as a marker gene, and by addition of a chromogenic substrate in the case of using a chromogenic enzyme gene as a marker gene.

The term "somatic cells" as used herein refers to all animal cells (preferably, cells of mammals including humans) excluding germ-line cells and totipotent cells, such as eggs, oocytes and ES cells. Examples of somatic cells include, but are not limited to: fetal somatic cells; neonatal somatic cells; and mature, healthy and diseased somatic cells; as well as primary cultured cells; subcultured cells; and established cell lines. Specific examples of somatic cells include: (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (such as skin cells), hair cells, hepatocytes, gastric mucosal cells, enterocytes, spleen cells, pancreatic cells (such as pancreatic exocrine cells), brain cells, lung cells, renal cells and adipocytes.

Further, in cases where iPS cells are used as a material for cells to be transplanted, it is preferable to use somatic cells whose HLA genotype is the same or substantially the same as that of the individual to be transplanted with the cells, in terms of avoiding rejection. The expression "substantially the same" as used herein means that the HLA genotype of the cells to be transplanted matches with that of the individual to be transplanted with the cells, to the extent that the immune reaction against the transplanted cells can be suppressed by an immunosuppressant. For example, somatic cells having matched HLA genotypes in three loci: HLA-A, HLA-B and HLA-DR, or in four loci further including HLA-C, are preferably used.

(E) ES Cells Derived from Cloned Embryo Obtained by Nuclear Transfer nt ES cells are ES cells derived from a cloned embryo produced by a nuclear transfer technique, and have almost the same properties as those of ES cells derived from a fertilized egg (T. Wakayama et al. (2001), Science, 292: pp. 740 to 743; S. Wakayama et al. (2005), Biol. Reprod., 72: pp. 932 to 936; and J. Byrne et al. (2007), Nature, 450: pp. 497 to 502). In other words, nt ES (nuclear transfer ES) cells are ES cells established from the inner cell mass of a blastocyst derived from a cloned embryo obtained by replacing the nucleus of an unfertilized egg with the nucleus of a somatic cell. For the production of nt ES cells, the combination of the nuclear transfer technique (J. B. Cibelli et al. (1998), Nature Biotechnol., 16: pp. 642 to 646) and the technique for producing ES cells (as described above) is used (Kiyoka Wakayama et al., (2008), Experimental Medicine, Vol 26, Issue 5 (special number), pp. 47 to 52). In the nuclear transfer, reprogramming can be achieved by introducing the nucleus of a somatic cell into an enucleated unfertilized egg of a mammal, followed by culturing for several hours.

<Mesodermal Progenitor Cells>

In the present invention, the term "mesoderm" includes germ layers constituted by cells capable of forming, during the process of development, the body cavity and mesothelium lining the body cavity, muscles, skeletons, dermis, connective tissues, heart and blood vessels (including vascular endothelium), blood (including blood cells), lymphatic vessels and spleen, kidney and ureter, and gonads (testis, uterus and gonadal epithelium). In the present invention, mesodermal progenitor cells are not distinguished from mesodermal cells, and are, for example, cells in which at least one marker gene selected from the group consisting of T (synonymous with Brachyury), KDR, FOXF1, FLK1, BMP4, MOX1 and SDF1 is expressed. Mesodermal progenitor cells are preferably cells which express T and KDR. The mesodermal progenitor cells produced in the present invention may be produced as a cell population containing other types of cells, and are preferably a cell population in which the mesodermal progenitor cells account for, for example, 50% or more, 60% or more, 70% or more, 80% or more, or 90% or more of the total cells in the population. The mesodermal progenitor cells can be produced, for example, by any of the method of the above described step (i), the method of Patent Document 4, the method of Non-patent Document 3 and the method of Non-patent Document 4, but the production method is not particularly limited thereto.

<Vascular Endothelial Cells>

In the present invention, vascular endothelial cells refer to thin flat cells constituting the inner surface of blood vessels. Vascular endothelial cells are not distinguished from endothelial progenitor cells in the present invention. Vascular endothelial cells in the present invention may be cells capable of forming a tubular structure, when continuously cultured, and more preferably, refer to cells capable of incorporating acetylated low-density lipoprotein (Ac-LDL). Vascular endothelial cells are characterized, for example, by the expression of markers such as KDR, CD34, and VE cadherin, but not particularly limited thereto. The vascular endothelial cells produced in the present invention may be produced as a cell population containing other types of cells, and are preferably a cell population in which the vascular endothelial cells account for, for example, 20% or more, 30% or more, 40% or more, 50% or more, 60% or more, 70% or more, 80% or more, or 90% or more of the total cells in the population. The differentiation-induced vascular endothelial cells can provide a useful culture model. In other words, the vascular endothelial cells produced by the method according to the present invention are useful as a model for a vascular disease caused by gene mutation.

Further, the vascular endothelial cells produced by the present method can be used for transplantation.

<Step (i): Step of Culturing Pluripotent Stem Cells in Culture Medium Comprising BMP, on Culture Vessel Coated with First Matrix, to Produce Mesodermal Progenitor Cells>

The step (i) is a step of performing an adhesion culture of pluripotent stem cells. In the present invention, the adhesion culture may be carried out by culturing the cells using a culture vessel which has been surface treated to be suitable for cell adhesion, or a culture vessel which has been coated with an extracellular matrix. The coating can be carried out by pouring a solution containing a matrix into a culture vessel, and then removing the solution as appropriate.

In the present invention, the term "matrix" refers preferably to an extracellular matrix. The extracellular matrix is a supramolecular architecture present extracellularly, and may be a naturally-derived or artificial (recombinant) substance. Examples thereof include substances such as collagen, proteoglycan, fibronectin, hyaluronic acid, tenacin, entactin, elastin, fibrillin and laminin; and fragments thereof. These extracellular matrices may be used in combination, or may be, for example, a preparation obtained from cells, such as extracellular matrix (Matrigel) derived from EHS mouse sarcoma cells.

In the present invention, "laminin" refers to a major cell adhesion molecule present in the basement membrane, which is a huge glycoprotein having a molecular weight of 800,000 Da, and is a heterotrimer composed of three subunit chains: $\alpha$ chain, $\beta$ chain and $\gamma$ chain. The three subunit chains associate with each other through their coiled-coil domains in the C-termini, and forms a stable heterotrimer molecule linked by disulfide bonds. For example, $\alpha$ chain is $\alpha1$, $\alpha2$, $\alpha3$, $\alpha4$ or $\alpha5$; $\beta$ chain is $\beta1$, $\beta2$ or $\beta3$; and $\gamma$ chain is $\gamma1$, $\gamma2$ or $\gamma3$, but not particularly limited thereto. Further, the laminin as used herein may be a fragment or a variant, and is not particularly limited as long as it is a fragment or a variant having an avidity for integrin. For example, the laminin fragment may be an E8 fragment obtained by digestion with elastase. Human-derived laminin is preferred.

The first matrix used in the step (i) is Matrigel, Type IV collagen, fibronectin, laminin-411 (a laminin composed of $\alpha4$ chain, ($\beta1$ chain and $\gamma1$ chain) or a fragment thereof, laminin-511 (a laminin composed of $\alpha5$ chain, ($\beta1$ chain and $\gamma1$ chain) or a fragment thereof, more preferably, Matrigel or laminin-511 or a fragment thereof, and still more preferably, E8 fragment of laminin-511 (laminin-511E8 (LM511E8); Ido et al. J. Biol. Chem. 282, pp. 11144 to 11154, 2007).

The BMP to be used in the step (i) is a BMP suitable for induction into mesodermal progenitor cells, and examples thereof include BMP2, BMP4 and BMP7. The BMP is more preferably BMP4. The BMP is preferably derived from a human.

The concentration of the BMP in the culture medium to be used in the step (i) is not particularly limited, as long as the concentration allows the induction into mesodermal progenitor cells. The concentration may be, for example, from 5 ng/ml to 200 ng/ml, from 10 ng/ml to 100 ng/ml, or from 20 ng/ml to 80 ng/ml. The concentration is preferably 80 ng/ml.

It is preferred that the culture medium to be used in the step (i) further contain a GSK3$\beta$ inhibitor and VEGF, in addition to the BMP.

In the present invention, the "GSK3$\beta$ inhibitor" is defined as a substance which inhibits the kinase activity (for example, an ability to phosphorylate $\beta$-catenin) of GSK-3$\beta$ protein, and many kinds of such substances are already known. Examples of the GSK3$\beta$ inhibitor include: BIO (also known as GSK-3$\beta$ inhibitor IX; 6-bromoindirubin-3'-oxime) which is an indirubin derivative; SB216763 (3-(2,4-dichlorophenyl)-4-(1-methyl-1H-indol-3-yl)-1H-pyrrol-2,5-dione) which is a maleimide derivative; GSK-3$\beta$ inhibitor VII (4-dibromoacetophenone) which is a phenyl a bromomethyl ketone compound; L803-mts (also known as GSK-3$\beta$ peptide inhibitor; Myr-N-GKEAPPAPPQpSP-NH$_2$ (SEQ ID NO: 1)) which is a cell membrane-permeable phosphorylated peptide; and CHIR99021 (6-[2-[4-(2,4-dichlorophenyl)-5-(4-methyl-1H-imidazol-2-yl)pyrimidin-2-ylamino]ethylamino]pyridine-3-carbonitrile) which has a high selectivity. These compounds are available from Calbiochem, Biomol and the like and can be easily used, but these may be obtained from other providers, or may be prepared from scratch. The GSK-3$\beta$ inhibitor to be used in the present invention may preferably be CHIR99021.

The concentration of CHIR99021 in the culture medium to be used in the step (i) is, for example, 1 nM, 10 nM, 50 nM, 100 nM, 500 nM, 750 nM, 1 $\mu$m, 2 $\mu$m, 3 $\mu$m, 4 $\mu$m, 5 $\mu$m, 6 $\mu$m, 7 $\mu$m, 8 $\mu$m, 9 $\mu$m, 10 $\mu$m, 15 $\mu$m, 20 $\mu$m, 25 $\mu$m, 30 $\mu$m, 40 $\mu$m, 50 $\mu$m, or a concentration therebetween, but not limited thereto. The concentration is preferably 4 $\mu$m.

The concentration of VEGF in the culture medium to be used in the step (i) is not particularly limited as long as the concentration allows the induction into mesodermal progenitor cells. The concentration may be, for example, from 5 ng/ml to 200 ng/ml, from 10 ng/ml to 100 ng/ml, or from 20 ng/ml to 80 ng/ml. The concentration is preferably 80 ng/ml. Human-derived VEGF is preferred.

The culture medium to be used in the step (i) can be prepared by using a medium used for culturing animal cells as the basal medium, and adding the BMP thereto as appropriate. Examples of the basal medium include Glasgow's Minimal Essential Medium (GMEM), IMDM medium, Medium 199, Eagle's Minimum Essential Medium (EMEM), $\alpha$-MEM medium, Dulbecco's modified Eagle's Medium (DMEM), Ham's F12 medium, RPMI 1640 medium, Fischer's medium, Neurobasal Medium (Life Technologies, Inc.), mTesR1 medium (Life Technologies, Inc.), Essential 8 (Life Technologies, Inc.), Stempro-34SFM medium (Life Technologies, Inc.) and combinations of these media. The medium may or may not contain serum. If necessary, the medium may contain, for example, one or more serum replacements such as albumin, transferrin, Knockout Serum Replacement (KSR) (serum replacement for FBS, for use in the culture of ES cells), N2 supplement (Invitrogen), B27 supplement (Invitrogen), fatty acids, insulin, collagen precursors, trace elements, 2-mercaptoethanol, 3'-thiolglycerol and/or the like; and may further contain one or more substances such as lipids, amino acids, L-glutamine, Glutamax (Invitrogen), non-essential amino acids, vitamins, growth factors, low molecular weight compounds, antibiotics, antioxidants, pyruvic acid, buffers, inorganic salts, and/or the like. A preferred basal medium is mTesR1 medium or Essential 8.

As to the culture conditions in the step (i), the culture temperature is from about 30 to 40° C., and preferably about 37° C., but not particularly limited thereto; and the culture is carried out under an atmosphere of $CO_2$-containing air, and the concentration of $CO_2$ is preferably from about 2 to 5%. The culture is carried out for a period of two days or more, and preferably from two days to three days.

<Step (ii): Step of Dissociating Cells into Single Cells>

The step (ii) is a step of substantially dissociating the cell population obtained in the step (i) into single cells. The dissociation of the cells can be achieved, for example, by a method in which cells are mechanically dissociated, or a method using a dissociation solution having a protease activity and a collagenase activity (such as Accutase (trademark), Accumax (trademark) etc.) or a dissociation solution having either a protease activity or a collagenase activity alone. Preferred method is one in which TrypLE Express (Life Technologies), which is a trypsin replacement, is used for dissociation of cells.

<Step (iii) or Step of Producing Vascular Endothelial Cells from Mesodermal Progenitor Cells (Hereinafter, Referred to as Step (iii) or the like): Step of Culturing Cells in Culture Medium Comprising VEGF, on Culture Vessel Coated with Second Matrix Selected from the Group Consisting of Laminin-411 or Fragment Thereof, Laminin-511 or Fragment Thereof, Matrigel, Type IV Collagen and Fibronectin>

The step (iii) or the like is a step of performing an adhesion culture of mesodermal progenitor cells. The method for producing the mesodermal progenitor cells to be used in the step (iii) or the like is not particularly limited. The mesodermal progenitor cells may be produced by the method according to the step (i), and the mesodermal progenitor cells may be cells which have been dissociated into single cells through the step (ii). The adhesion culture can be carried out using any of the matrices described in the step (i). However, the matrix to be used in the step (iii) or the like is preferably Matrigel, type IV collagen, fibronectin, laminin-411 or a fragment thereof, or laminin-511 or a fragment thereof, and more preferably a fragment of laminin-411. The fragment of laminin-411 is a fragment having an avidity for integrin α6β1, and more preferably E8 fragment of laminin-411(laminin-411 E8: LM411E8). The definition of laminin herein may include a variant thereof, but does not include a variant (laminin-411 E8 (EQ)) which has lost its avidity for integrin α6β1 due to the glutamic acid at the third position from the C terminus of the γ chain of laminin-411 E8 being substituted with glutamine.

The culture medium to be used in the step (iii) or the like can be prepared by using a medium used for culturing animal cells as the basal medium, and adding VEGF thereto as appropriate. Examples of the basal medium include Glasgow's Minimal Essential Medium (GMEM), IMDM medium, Medium 199, Eagle's Minimum Essential Medium (EMEM), α-MEM medium, Dulbecco's modified Eagle's Medium (DMEM), Ham's F12 medium, RPMI 1640 medium, Fischer's medium, Neurobasal Medium (Life Technologies, Inc.), mTesR1 medium (Life Technologies, Inc.), Essential 8 (Life Technologies, Inc.), Stempro-34SFM medium (Life Technologies, Inc.), Endothelial Serum Free Medium (Life Technologies) and combinations of these media. The medium may or may not contain serum. If necessary, the medium may contain, for example, one or more serum replacements such as albumin, transferrin, Knockout Serum Replacement (KSR) (serum replacement of FBS for use in the culture of ES cells), N2 supplement (Invitrogen), B27 supplement (Invitrogen), fatty acids, insulin, collagen precursors, trace elements, 2-mercaptoethanol, 3'-thiolglycerol and/or the like; and may further contain one or more substances such as lipids, amino acids, L-glutamine, Glutamax (Invitrogen), non-essential amino acids, vitamins, growth factors, low molecular weight compounds, antibiotics, antioxidants, pyruvic acid, buffers, inorganic salts, and/or the like. A preferred basal medium is Stempro-34SFM medium or Endothelial Serum Free Medium (Life Technologies).

The concentration of VEGF in the culture medium used in the step (iii) or the like is not particularly limited as long as the concentration allows the induction into vascular endothelial cells. The concentration may be, for example, from 5 ng/ml to 200 ng/ml, from 10 ng/ml to 100 ng/ml, or from 20 ng/ml to 80 ng/ml. The concentration is preferably 80 ng/ml.

As to the culture conditions in the step (iii) or the like, the culture temperature is from about 30 to 40° C., and preferably about 37° C., but not particularly limited thereto; and the culture is carried out under an atmosphere of $CO_2$-containing air, and the concentration of $CO_2$ is preferably from about 2 to 5%. The culture is carried out for a period of two days or more, preferably from four days to seven days, and particularly preferably four days.

<Revascularizing Agent>

The vascular endothelial cells obtained in the present invention can be administered for treating patients with severe ischemic diseases including coronary artery diseases and lower limb ischemic diseases (such as Buerger's disease, obstructive arteriosclerosis, etc.). In other words, the transplantation of the thus obtained vascular endothelial cells to ischemic sites can be performed as a revascularization therapy (Takayuki Asahara, YAKUGAKU ZASSHI 127 (5), pp. 841 to 845, 2007). Accordingly, the present invention provides a revascularizing agent containing the vascular endothelial cells obtained from pluripotent stem cells according to the above described method.

<Screening Method>

The present invention provides a screening method for a therapeutic agent for treating severe ischemic diseases including coronary artery diseases and lower limb ischemic diseases (such as Buerger's disease, obstructive arteriosclerosis, etc.), the method including the following steps;

(i) a step of bringing a candidate drug into contact with the vascular endothelial cells obtained by the above described method;

(ii) a step of measuring the dysfunction of the vascular endothelial cells; and (iii) a step of selecting the candidate drug as a therapeutic agent for treating severe ischemic diseases, if the candidate drug decreases the dysfunction of the vascular endothelial cells as compared to that of the vascular endothelial cells which are not brought into contact with the candidate drug.

In the present invention, examples of the dysfunction of vascular endothelial cells include: an increase in oxidative stress such as the expression of NO synthase or production of NO; an increase in the expression of endothelial cell adhesion molecules; an increase in the production of angiotensin II, endothelin-1 and plasminogen activator-inhibitor-1; and an increase in the amount of uptake of lipids such as Ac-LDL.

In the present invention, examples of candidate drugs include cell extracts, cell culture supernatants, microbial fermentation products, extracts derived from marine organisms, plant extracts, purified proteins and crude proteins, peptides, non-peptide compounds, synthetic low molecular weight compounds, and natural compounds.

In the present invention, the candidate drugs can be obtained using any of numerous approaches in combinatorial library methods known in the art, including: (1) the biological library method; (2) the synthetic library method using deconvolution; (3) the "one-bead one-compound" library method; and (4) the synthetic library method using affinity chromatography selection. Application of the biological library method using affinity chromatography selection is limited to peptide libraries, but the other four approaches can be applied to low molecular weight compound libraries of peptides, non-peptide oligomers or compounds (Lam (1997) Anticancer Drug Des. 12: pp. 145 to 167). Examples of methods for synthesizing molecular libraries can be found in the art (DeWitt et al. (1993) Proc. Natl. Acad. Sci. USA 90: pp. 6909 to 6913; Erb et al. (1994) Proc. Natl. Acad. Sci. USA 91: pp. 11422 to 11426; Zuckermann et al. (1994) J. Med. Chem. 37: pp. 2678 to 2685; Cho et al. (1993) Science 261: pp. 1303 to 1305; Carell et al. (1994) Angew. Chem. Int. Ed. Engl. 33: p. 2059; Carell et al. (1994) Angew. Chem. Int. Ed. Engl. 33: p. 2061; and Gallop et al. (1994) J. Med. Chem. 37: pp. 1233 to 1251). The compound libraries can be prepared as solutions (see Houghten (1992) Bio/Techniques 13: pp. 412 to 421) or beads (Lam (1991) Nature 354: pp. 82 to 84), chips (Fodor (1993) Nature 364: pp. 555 to 556), bacteria (U.S. Pat. No. 5,223,409), spores (U.S. Pat. Nos. 5,571,698, 5,403,484, and 5,223,409), plasmids (Cull et al. (1992) Proc. Natl. Acad. Sci. USA 89: pp. 1865 to 1869) or phages (Scott and Smith (1990) Science 249: pp. 386 to 390; Devlin (1990) Science 249: pp. 404 to 406; Cwirla et al. (1990) Proc. Natl. Acad. Sci. USA 87: pp. 6378 to 6382; Felici (1991) J. Mol. Biol. 222: pp. 301 to 310; and US Patent Application No. 2002/103360).

<Kit>

Another embodiment of the present invention includes a kit for producing vascular endothelial cells from pluripotent stem cells. The kit includes culture media, additives, culture vessels and/or the like to be used in the respective steps for producing the above described vascular endothelial cells. The kit may be, for example, a kit including one or more reagents selected from the group consisting of matrices (preferably, laminin-411 E8), BMP4, VEGF and GSK3β inhibitors. The kit may further include a document or an instruction which describes the procedure of the production process.

The present invention will now be described more specifically, with reference to the following Examples. However, the present invention is in no way limited by these Examples.

EXAMPLES

Cells and Culture

Human ES cells (KhES1) were obtained from Institute for Frontier Medical Sciences, Kyoto University, and cultured according to a conventional method (Suemori H, et al. Biochem Biophys Res Commun. 345: pp. 926 to 932, 2006). Human iPS cells (253G4, 409B2 and 223Q5) were obtained from Professor Yamanaka of Kyoto University.

The maintenance culture of the human ES cells and the human iPS cells were carried out on SNL feeder cells, using an ES medium (ReproCELL) supplemented with 5 mg/mL of bFGF (Wako). SNL feeder cells are available from DS Pharma Biomedical Co., Ltd. and the like. The subculture was carried out by treating the cells with a CTK solution (0.25% trypsin (Life Technologies), 0.1% collagenase IV (Life Technologies), 20% KSR, and 1 mM CaCl$_2$) for about 30 seconds at room temperature to dissociate the cells into single cells, and the SNL cells were removed by a known method (Suemori, H. et al. Biochemical and Biophysical Research Communications 345, 926932 (2006)).

Preparation of LM411E8 Fragment

For the expression of LM411E8, expression vectors for α4 chain E8 fragment, β1 chain E8 fragment, and γ1 chain E8 fragment were transfected into human kidney-derived 293F cells (Invitrogen) in accordance with the method described by Ido et al. (Ido H, et al., J. Biol. Chem., 282, pp. 11144 to 11154, 2007).

Preparation of Expression Vector for Human Laminin α4 Chain E8 Fragment

For the preparation of a cDNA fragment encoding a mouse Ig-κ chain V-J2-C signal peptide, a 6× His tag, and α4 chain E8 fragment in this order from the 5' end, a cDNA fragment encoding a mice Ig-κ chain V-J2-C signal peptide and a 6× His tag, and a cDNA fragment encoding α4 chain E8 were separately obtained, and these two types of fragments were ligated and amplified by extension PCR.

First, PCR was performed using a human laminin α5 chain E8 expression vector (Ido et al., J. Biol. Chem., 282, pp. 11144 to 11154, 2007) as a template, and using the following primer sets (i), to amplify the region corresponding to the mouse Ig-κ chain V-J2-C signal peptide and the 6×His tag. The reverse primer contains a sequence used for extension PCR at the 5'-end.

(i) Primers for Amplification of Signal Peptide Sequence and 6× His Tag Sequence

```
                                    (forward, SEQ ID NO: 2)
5'-GAGGTCTATATAAGCAGAGCTCTCTGGCTAACTA-3'

(reverse, SEQ ID NO: 3)
5'-CATTGGCTTCATCATGATGATGATGATGAAGC-3'
```

Next, PCR was performed using a plasmid (Hayashi et al., Biochem Biophys Res Commun., 299, pp. 498 to 504, 2002) containing a full-length cDNA sequence of human laminin α4 chain as a template, to amplify the region corresponding to the α4 chain (Glu629-His1449, Accession No.: NP 002281). The forward primer contains a sequence used for extension PCR at the 5'-end, and the reverse primer contains an EcoRI recognition sequence at the 5'-end.

(ii) Primers for Amplification of Laminin α4 Chain E8 Sequence

```
                                    (forward, SEQ ID NO: 4)
5'-CATCATGATGAAGCCAATGAAACAGCAGAATTTGC-3'

(reverse, SEQ ID NO: 5)
5'-GCAGAATTCTCAATGAGAGTTTCTTGGAGTATTCC-3'
```

The thus obtained two types of cDNA fragments were ligated and amplified by extension PCR, to obtain a cDNA fragment encoding a mouse Ig-κ chain V-J2-C signal peptide, a 6× His tag and α4 chain E8. The amplified cDNA was digested with restriction enzymes HindIII and EcoRI, and the digested fragment was inserted into the corresponding site in a mammalian cell expression vector, pSecTag2B (Invitrogen), to prepare an expression vector for human α4 chain E8 fragment (containing a 6× His tag at the N-terminus side).

The expression vectors for human β1 chain E8 fragment (containing an HA tag at the N-terminus side), and for human γ1 chain E8 fragment (containing a FLAG tag at the N-terminus side) were prepared according to the method described by Ido et. al. (Ido H, et al., J. Biol. Chem., 282, pp. 11144 to 11154, 2007).

The thus prepared expression vectors for respective chains were transfected into the human kidney-derived 293F cells to prepare LM411E8. Specifically, a quantity of 400 μg each of the expression vectors for the respective chains were transfected simultaneously into 1,000 ml of the 293F cells ($1.0\times10^6$ cells/ml), using a transfection reagent 293 fectin (trademark; Life Technologies) and Opti-MEM I (registered trademark; Invitrogen). The cells were cultured for 72 hours, and then the culture medium was collected. The collected culture medium was centrifuged at 1,000×g for 10 minutes, and the resulting supernatant was further centrifuged at 15,000×g for 30 minutes, to remove remaining cells and insoluble matter. To the resulting culture supernatant, PMSF (final concentration: 1 mM) and sodium azide (final concentration: 0.02%) were added, followed by mixing thoroughly. Subsequently, 15 ml of Ni-NTA agarose (Qiagen) was added to the culture supernatant, and the resultant was incubated overnight, so as to allow the protein of interest to bind thereto. The Ni-NTA agarose was collected, washed with TBS(−) (tris-buffered saline without Ca or Mg), and then eluted with 200 mM of imidazole/TBS(−). The A280 values of eluted fractions were confirmed by a spectrophotometer, and 5 ml of ANTI-FLAG M2 affinity Gel (Sigma) was added to the fraction with a high A280 value, followed by rotating the resulting mixture at 4° C. overnight. The affinity gel was transferred to an Econo Column, washed with TBS(−), and then eluted with 100 g/ml of TBS(−) containing FLAG peptide (registered trademark; Sigma). The eluted fractions were confirmed by CBB staining, and the LM411E8-eluted fractions were combined and dialyzed against PBS(−) (phosphate buffered saline without Ca or Mg).

Coating

Laminin-411 (LM411) (Biolamina) and Laminin-511 (LM511) (Biolamina) were each diluted with PBS(−) to a concentration of 20 µg/mL, and dispensed into culture dishes at a concentration of 2 µg/cm². GFR-Matrigel (BD Biosciences) was diluted with PBS(−) to a concentration of 200 µg/mL on ice, and dispensed into culture dishes at a concentration of 20 µg/cm². Type IV collagen (BD Biosciences) was diluted with 0.05 M hydrochloric acid to a concentration of 100 µg/mL, and dispensed into culture dishes at a concentration of 10 µg/cm² concentration. Fibronectin (Millipore) was diluted with PBS(−) to a concentration of 20 µL/mL, and dispensed into culture dishes at a concentration of 2 µg/cm². LM511E8 fragment (Nippi) and LM411E8 were each diluted with PBS(−) to a concentration of 4 µL/mL, and dispensed into culture dishes at a concentration of 0.4 µg/cm².

The resulting culture dishes after the dispensing were incubated for two hours at 37° C., to carry out the coating of each of the above coating agents.

Example 1

Induction of Differentiation from Pluripotent Stem Cells into Mesodermal Progenitor Cells The induction of differentiation from the pluripotent stem cells into mesodermal progenitor cells was carried out according to the method described by Niwa et al., (Niwa A, et al, PLoS One. 6: e22261 2011, Yanagimachi M D, et al, PLoS One. 8: e59243, 2013). Specifically, colonies of the pluripotent stem cells were seeded on a plate coated with GFR-Matrigel, at a density of 2 colonies/cm², followed by culturing in mTeSR1 medium (STEMCELL TECHNOLOGIES). The cells were allowed to grow until the diameters of the colonies were about 750 µm, and then the medium was replaced with mTeSR1 medium containing 20 ng/mL of BMP4 (R&D systems), followed by culturing for three days (corresponds to Day 3 in FIG. 1).

Induction of Differentiation from Mesodermal Progenitor Cells to Endothelial Cells The medium of the culture containing the thus obtained mesodermal progenitor cells was replaced with Stempro-34SFM (Life Technologies) containing 40 ng/mL of VEGF (R&D systems), and the cells were cultured for another four days (corresponds to Day 7 in FIG. 1).

Extraction and Confirmation of Functions of Vascular Endothelial Cells

Figure 2:
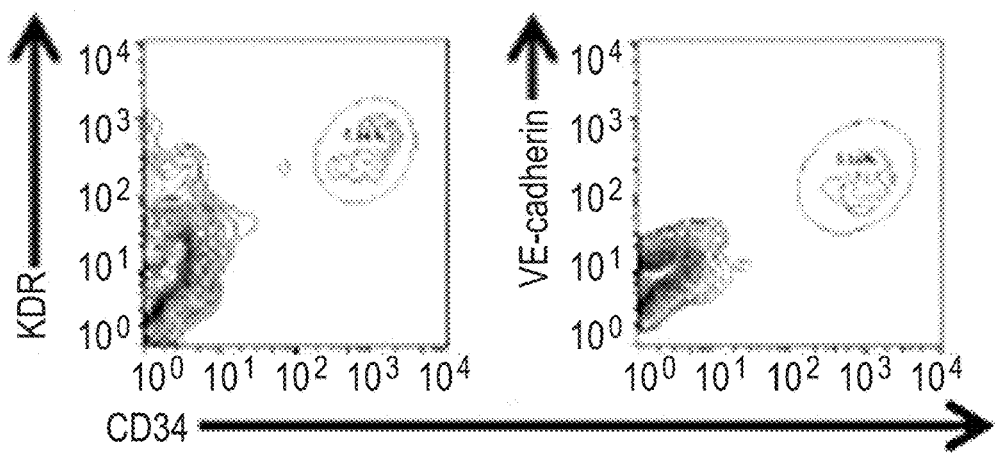
FIG. 2 shows the results (halftone images) obtained by analyzing the expression of KDR, CD34 and VE-Cadherin by flow cytometry, in the cells on Day 7 from the start of differentiation induction.

The expression of markers on Day 7 after the induction of differentiation was analyzed by flow cytometry. Specifically, the resulting cells were treated with TrypLE Express at 37° C. for 20 minutes, and an antibody reaction was carried out in Stempro-34 medium. An anti-human KDR antibody (Biolegend), an anti-human CD34 antibody (Beckman coulter), and an anti-human VE-cadherin antibody (eBioscience) were each diluted at 1:100 before use. As a result, the expression of KDR/CD34NE-cadherin was observed in about 10% of the cells (FIG. 2).

Figure 3:
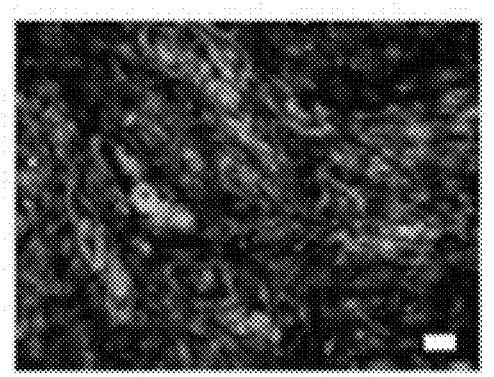
FIG. 3 shows an image (photograph) stained for CD31 (green), incorporated acetylated low-density lipoprotein (Ac-LDL) (red) and DAPI (blue), in the cells on Day 10 from the start of differentiation induction.

Next, on Day 10 of continued culture after the induction of differentiation, CD34$^+$/VE-cadherin$^+$ fractions were extracted, and an Ac-LDL uptake assay and immunostaining were carried out. Specifically, DiI-Ac-LDL (Life Technologies) was added to Endothelial Serum Free Medium (Life Technologies) at a dilution ratio of 1:100, and allowed to react with the resulting cells for five hours under the conditions of 37° C. and 5% $CO_2$. Thereafter, the cells were washed twice with PBS(−) and fixed using Cytofix (BD Biosciences). The fixation of cells was carried out at room temperature for five minutes. Subsequently, blocking was carried out at room temperature for 30 minutes using Perm/Wash (BD Biosciences), and the cells were allowed to react with an anti-human CD31 antibody (R&D systems) (1:10) at 4° C. overnight. After washing twice with Perm/Wash, the secondary antibody reaction (FITC-labeled anti-sheep IgG antibody, Jackson immunoresearch, 1:100) was allowed to proceed at room temperature for one hour. Subsequently, the cells were washed twice with Perm/Wash, and imaged by a fluorescence microscope (Keyence). As a result, the expression of CD31, which is a marker of vascular endothelial cells, and Ac-LDL uptake, which is one of the functions of vascular endothelial cells, were observed (FIG. 3). Above described results suggest that the induced CD34$^+$/VE-cadherin$^+$ cells are vascular endothelial cells.

Effect of Subculture before Stimulation with VEGF

Figure 4:
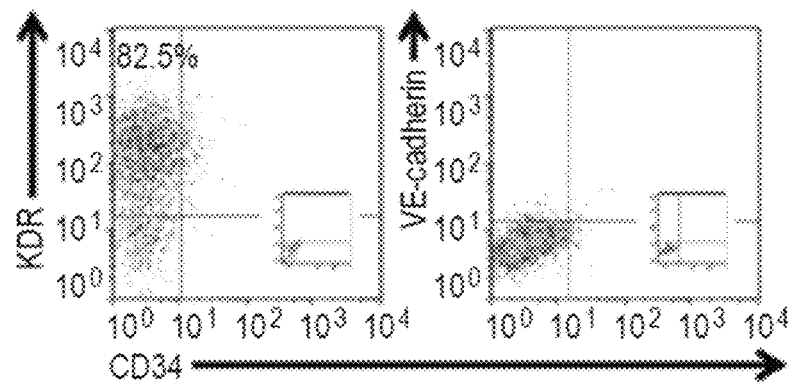
FIG. 4 shows the results (halftone images) obtained by analyzing the expression of KDR, CD34 and VE-Cadherin by flow cytometry, in the cells on Day 3 from the start of differentiation induction.

Although 80% or more of the KDR-positive mesodermal progenitor cells appeared by Day 3 after the induction of differentiation (FIG. 4), only a small number of cells differentiated into vascular endothelial cells thereafter, even stimulated with VEGF. Thus, for the purpose of eliminating the intercellular interaction which had been formed by Day 3, the cells were treated with TrypLE Express (Life Technologies) at 37° C. for 20 minutes to be dissociated into single cells, after being cultured with BMP/Matrigel and immediately before being stimulated with VEGF. The resulting single cells were allowed to differentiate again by plate culture (VEGF/Matrigel). As a result, an increase in the purity of the CD34$^+$/VE-cadherin$^+$ cells was observed in the group in which the cells had been dissociated into single cells (passage group), (FIG. 5).

Induction of Differentiation Using Single Matrix Plate

Figure 5:
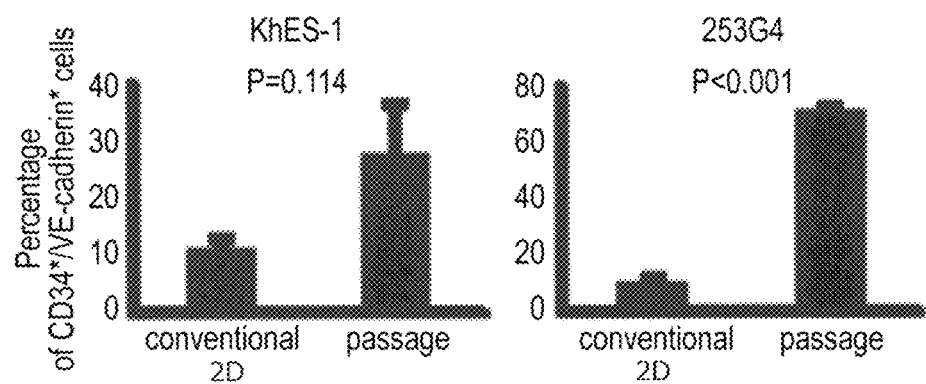
FIG. 5 shows graphs of the contents in percentage of CD34-positive and VE-Cadherin-positive cells in the group (passage) which were passaged and the group (conventional 2D) which were not passaged, when inducing the differentiation of ES cells (KhES-1) and iPS cells (253G4, 409B2 and 223Q5) into endothelial cells.
Figure 5:
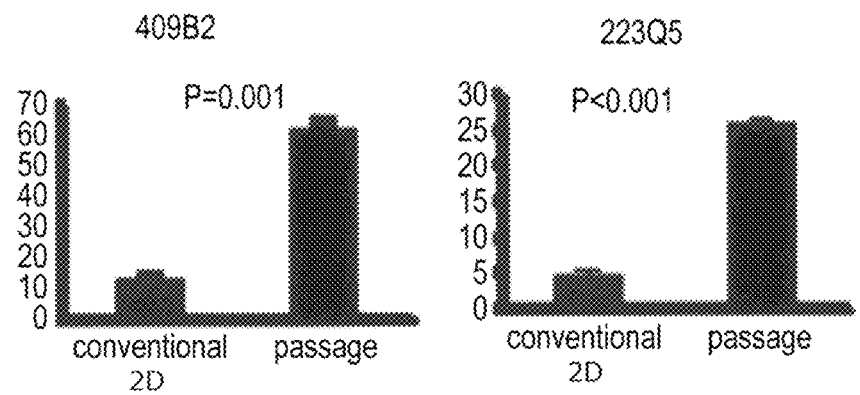
Figure 6:
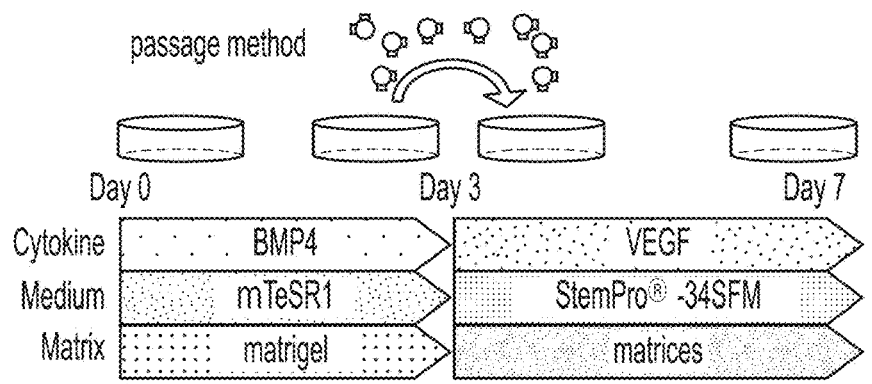
FIG. 6 shows an improved scheme for inducing the differentiation into vascular endothelial cells.
Figure 7:
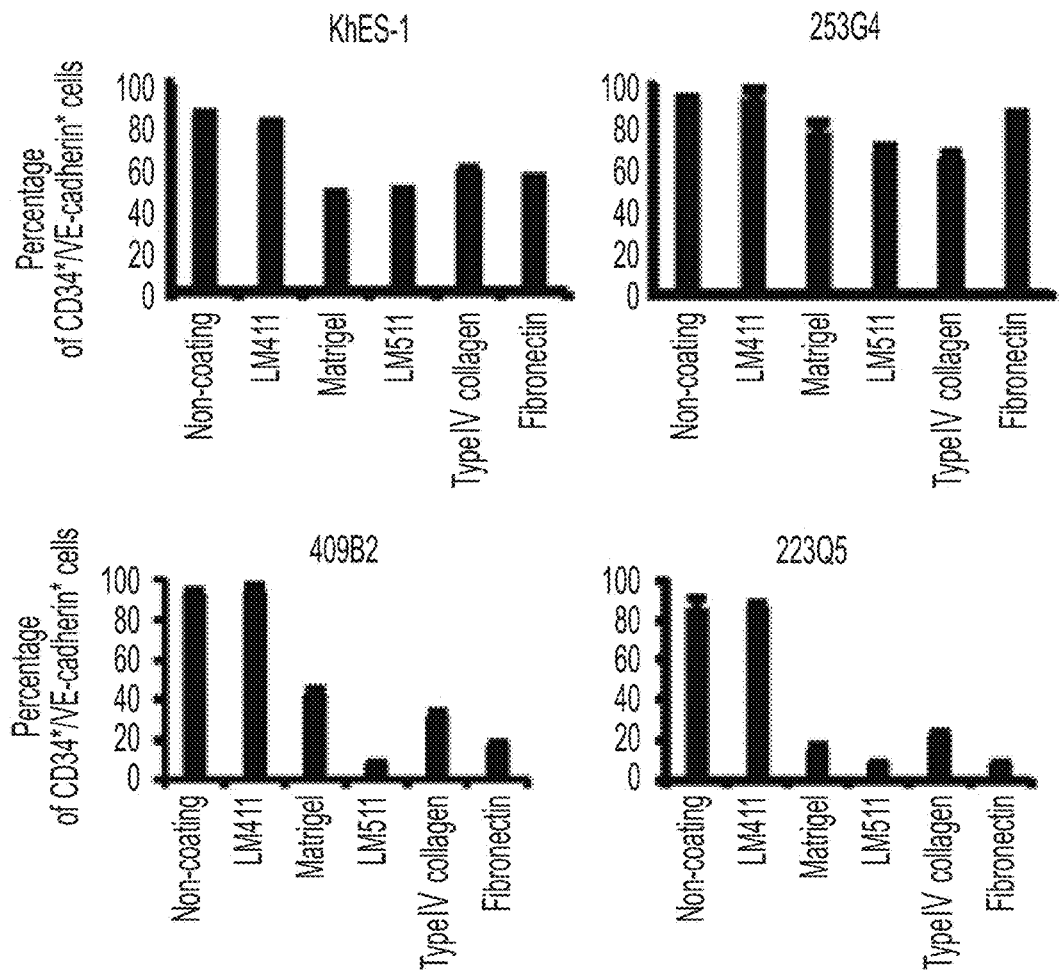
FIG. 7 shows graphs of the contents in percentage of CD34-positive and VE-Cadherin-positive cells in the case of using an uncoated culture vessel (Non-coating) and the cases of using culture vessels coated with respective second matrices (LM411, Matrigel, LM511, Type IV collagen and Fibronectin), when inducing the differentiation of ES cells (KhES-1) and iPS cells (253G4, 409B2 and 223Q5) into endothelial cells.

Although an increase in the purity of the CD34$^+$/VE-cadherin$^+$ cells was observed by carrying out the dissociation of the cells on Day 3, as described above, the effect of increasing the purity varied depending on the cell lines (FIG. 5). Therefore, induction of differentiation was carried out using second matrix plates coated with various types of single matrix proteins (from Day 3 to Day 7), in order to search for a matrix which allows for the induction into vascular endothelial cells at a high purity, and in a stable manner across the cell lines. The method for differentiation induction is shown in FIG. 6. As a result, it has been demonstrated that vascular endothelial cells can be induced at a high purity in each of the cell lines, in the case of using a non-coated plate (non-coating) and a plate coated with LM411. (FIG. 7). On the other hand, in the case of using LM511, which has been considered to be useful for the maintenance of pluripotent stem cells, a decrease in the purity was observed in some of the cell lines. Further, the comparison of the yields of the obtained vascular endothelial cells revealed that the use of LM411 provided a higher yield.

Figure 8:
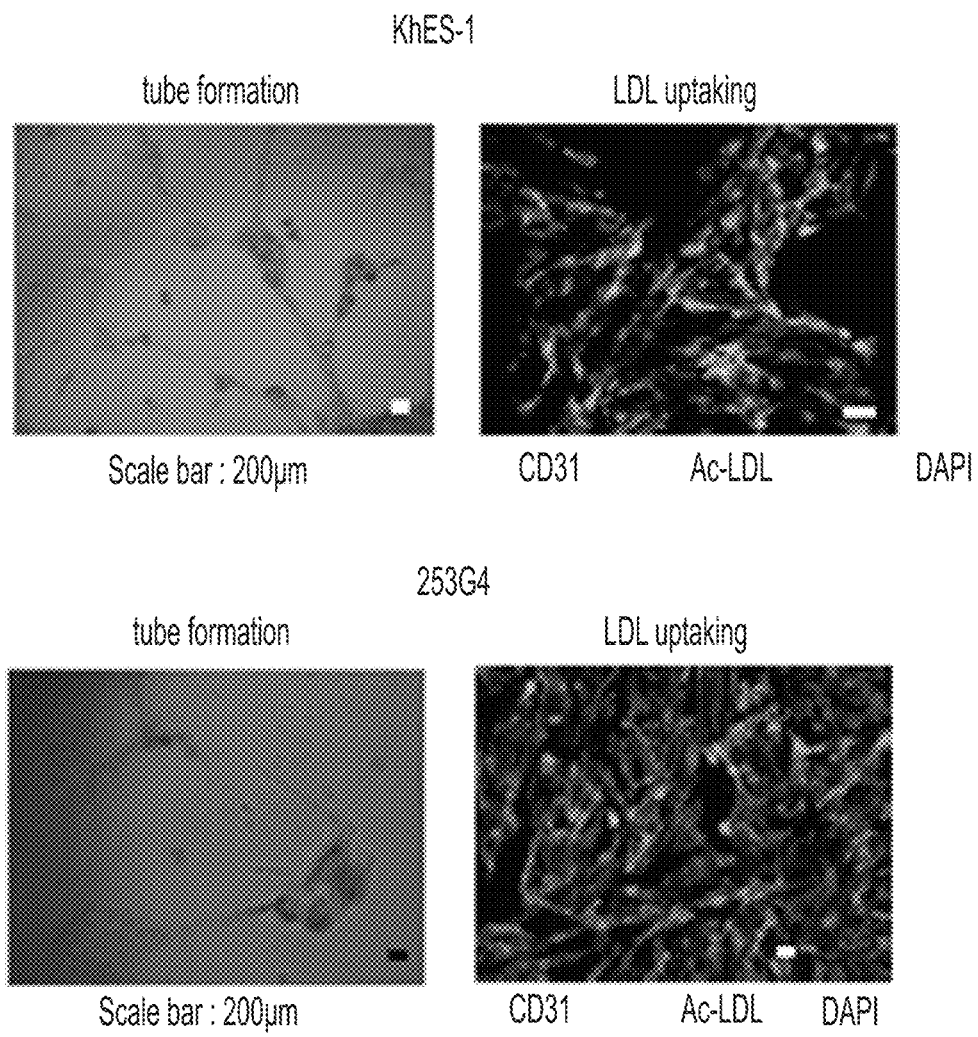
FIG. 8 shows photographs of: phase-contrast images (left) obtained by observing the tube formation of endothelial cells induced from ES cells (KhES-1) and iPS cells (253G4); and images (right) stained for CD31 (green), incorporated Ac-LDL (red) and DAPI (blue).

In addition, an Ac-LDL uptake assay and a tube formation assay were carried out in order to evaluate the function of the vascular endothelial cells obtained using LM411. The tube formation assay was carried out by the following method. Matrigel (BD Biosciences) was dispensed into wells of a 96 well plate in an amount of 50 μL/well, and allowed to solidify by being left to stand at 37° C. for 30 minutes. Subsequently, the cells were suspended in Endothelial Serum Free Medium, and to the resultant, VEGF was added to a concentration of 80 ng/mL. The resulting cell suspension was dispensed on the solidified Matrigel at a cell density of $4\times10^4$ cells/well, followed by culturing under the conditions of 37° C. and 5% $CO_2$ overnight (Kurian L, et al., Nat. Methods. 10: pp. 77 to 83, 2013). As a result, it has been confirmed that the vascular endothelial cells induced by using LM411 have a tube formation ability and Ac-LDL uptake capacity (FIG. 8). The above results has confirmed that it is possible to efficiently induce vascular endothelial cells by dissociating mesodermal progenitor cells into single cells and then culturing the cells on a plate coated with LM411.

Improvement in Yield by Use of Laminin-411 E8 Fragment

Subsequently, the effect of the use of LM411E8, which is a fragment of LM411 including an integrin-binding site, on the adhesion activity and differentiation of the mesodermal progenitor cells were examined. Specifically, colonies of the pluripotent stem cells were seeded on a plate coated with GFR-Matrigel, at a density of 2 colonies/cm², followed by culturing in mTeSR1 medium (STEMCELL TECHNOLOGIES). The cells were allowed to grow until the diameters of the colonies were about 750 μm, and then the medium was replaced with mTeSR1 medium containing 80 ng/mL of BMP4 (R&D systems). After culturing for three days, the cells were treated with TrypLE Express (Life Technologies) at 37° C. for 20 minutes to be dissociated into single cells, and suspended in Stempro-34SFM (Life Technologies) medium containing 80 ng/mL VEGF (R&D systems). The suspended cells were seeded on a plate coated with LM411E8 at a density of $4\times10^4$ cells/cm², followed by culturing for another four days.

Figure 9:
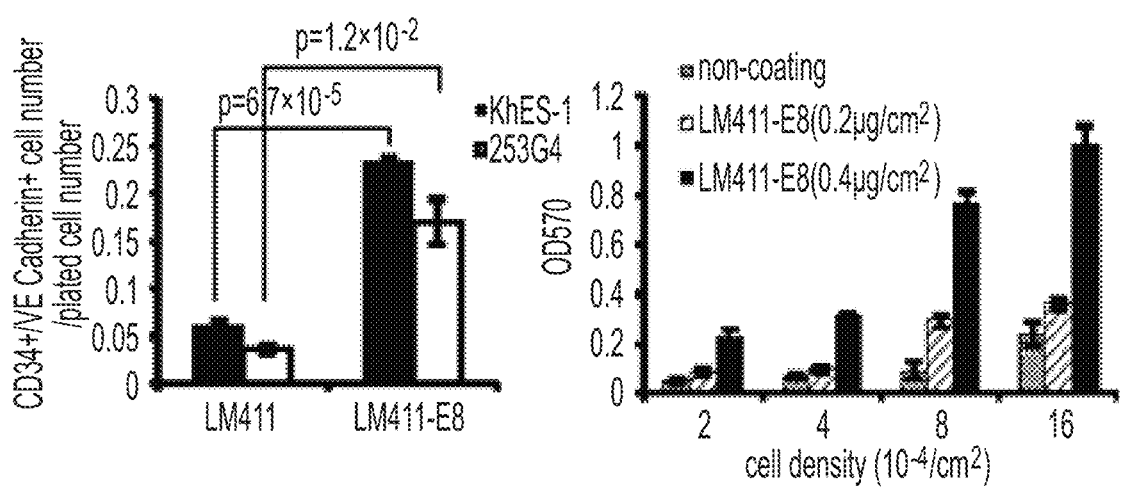
FIG. 9 shows graphs of: the ratio of the number of CD34 positive and VE-Cadherin positive cells to the total number of adhered cells, when the induction of differentiation was carried out using LM411 or LM411E8 (left); and the fluorescence intensity (number of vascular endothelial cells) at each concentration of LM411E8 in ES cells (KhES-1) (0 (non-coating), 0.2 $\mu g/cm^2$ or 0.4 $\mu g/cm^2$) and each cell seeding density (right).

As a result, when LM411E8 was used, vascular endothelial cells were obtained at a purity almost the same as that in the case of using LM411, and the cell yield was higher than that in the case of using LM411 (the graph on the left in FIG. 9). Further, the number of the resulting vascular endothelial cells increased in a manner dependent on the concentration of LM411E8 (the graph on the right in FIG. 9).

Figure 10:
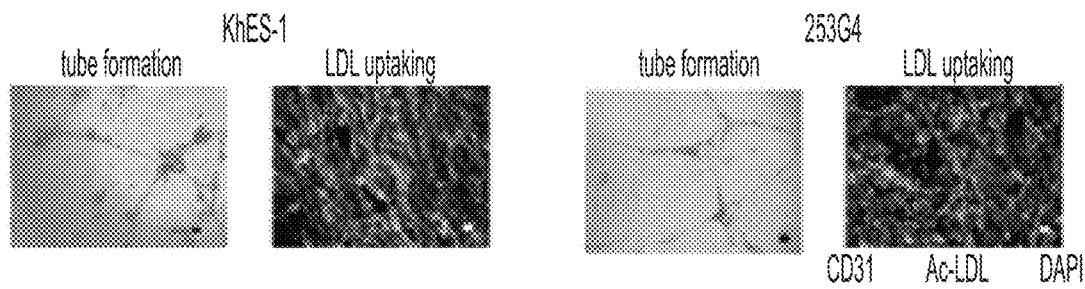
FIG. 10 shows photographs of: phase-contrast images (left) obtained by observing the tube formation of endothelial cells induced from ES cells (KhES-1) and iPS cells (253G4) using LM411E8; and images (right) stained for CD31 (green), incorporated Ac-LDL (red) and DAPI (blue).

In addition, it has been confirmed that the vascular endothelial cells differentiated by using LM411E8 have a tube formation ability and Ac-LDL uptake capacity (FIG. 10).

Figure 11:
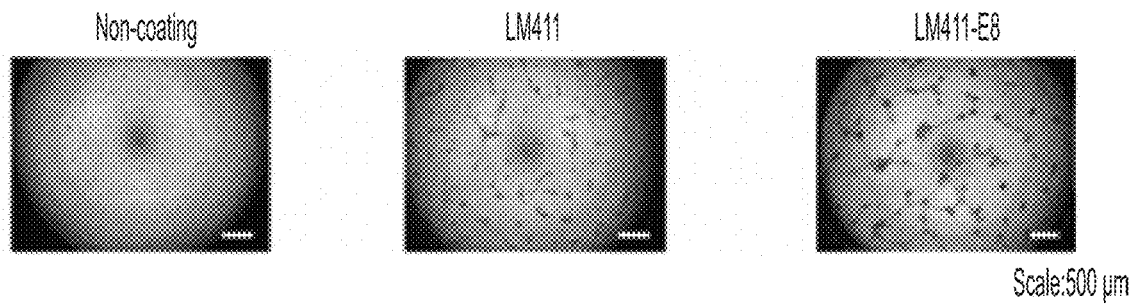
FIG. 11 shows photographs of phase-contrast images obtained by observing the tube formation of vascular endothelial cells whose differentiation was induced using: a non-coated culture vessel, Non-coating (left); a culture vessel coated with LM411 (middle); or a culture vessel coated with LM411E8 (right).
Figure 12:
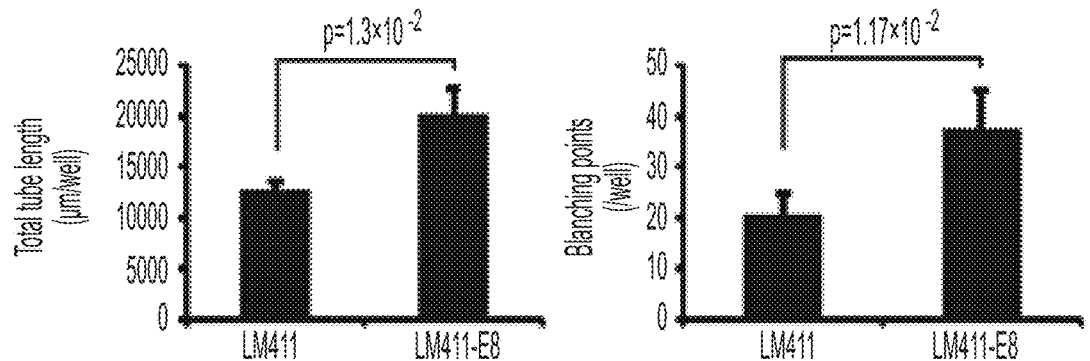
FIG. 12 shows graphs of: the length (left); and the number of branches in the tubes (right); of the tubes derived from vascular endothelial cells whose differentiation was induced using LM411 or LM411E8.

The comparison of the vascular endothelial cells differentiated by using the non-coated plate (non-coating), the plate coated with LM411E8 or LM411 revealed that no tube formation was observed in the cells differentiated under the non-coating condition, and that the cells differentiated by using LM411E8 formed tubes with a higher length and a higher number of branches as compared to the tubes formed by the cells differentiated using LM411 (FIG. 11 and FIG. 12). The above results have demonstrated that it is possible to obtain vascular endothelial cells having a higher functionality, by inducing differentiation using LM411E8.

The gene expression profiles of the endothelial cells differentiated under the above described three conditions were analyzed by single cell microarray analysis using RNA-sequencing. As a result, it has been shown that the expression profiles of these cells were similar to that of human umbilical vein endothelial cells (HUVEC). Further, a subsequent clustering analysis has revealed that the cells differentiated by using LM411E8 have a gene expression profile different from those differentiated under the non-coating condition and those differentiated by using LM411. In particular, it has been confirmed that the gene expression related to the response to the stimulation by VEGF and to angiogenesis are enhanced by the use of LM411E8.

Interaction between Mesodermal Progenitor Cells Derived from Pluripotent Stem Cells and LM411E8

An increase in the yield of endothelial cells by the use of LM411E8 is thought to result from the adhesion activity of the cells. Therefore, the adhesion activities of the mesodermal progenitor cells on Day 3 after the induction of differentiation to the non-coated plate (non-coating), the plate coated with LM411 or the plate coated with LM411E8 were compared. As a result, the cell adhesion to LM411E8 was markedly higher as compared to the other two.

LM411 is known to bind to integrin α6β1 and α7×1β1. Therefore, the mesodermal progenitor cells on Day 3 after the induction of differentiation were subjected to a cell adhesion assay, using a neutralizing antibody against integrin α6β1. As a result, the number of adhered cells decreased almost to the same degree as that of the cells differentiated under the non-coating condition. LM411E8 (EQ) is a variant of LM411E8 which has lost its avidity for integrin α6β1 due to the glutamic acid at the third position from the C terminus of the γ chain being substituted with glutamine. The avidity for the above described LM411E8 (EQ) of the mesodermal progenitor cells on Day 3 after the induction of differentiation was evaluated, and the results indicated that the avidity was almost the same as that of the cells differentiated under the non-coating condition. Based on the above results, the initial adhesion to LM411E8 of the mesodermal progenitor cells on Day 3 after the induction of differentiation is thought to be dependent on integrin α6β1.

Function of LM411-E8

Figure 13:
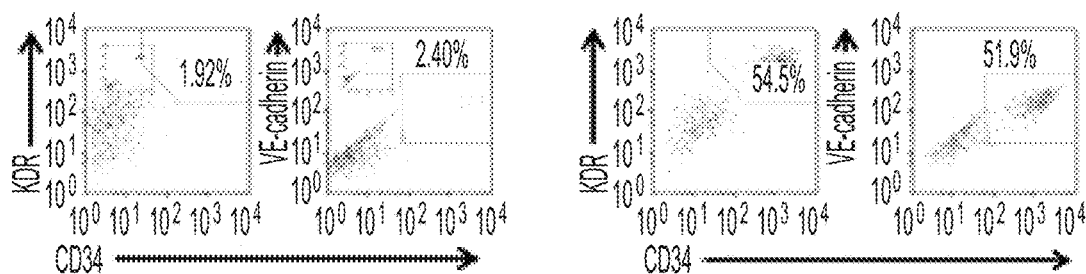
FIG. 13 shows the results (halftone images) obtained by analyzing, by flow cytometry, the expression of KDR, CD34 and VE-Cadherin in vascular endothelial cells whose differentiation was induced by double switching the matrices (from LM411 to Matrigel (left) or from LM411 to LM411 (right)).

In order to investigate whether LM411 is responsible for selecting the cells to be differentiated into vascular endothelial cells, or enhancing the vascular endothelial differentiation of the cells adhered thereto, a double-switching assay was carried out. In the double-switching assay, the mesodermal progenitor cells obtained on Day 3 after the induction of differentiation using BMP4/Matrigel were dissociated into single cells and then seeded on a plate coated with LM411, and the cells adhered thereto were subcultured again on Matrigel (MG) or LM411. As a result, the use of LM411-MG resulted in a significant decrease in the purity as compared to the case of using LM411-LM411 (FIG. 13). Based on the above, it is thought that LM411 is not only responsible for selecting the cells in a receptor specific manner, but also has an impact on the subsequent vascular endothelial differentiation of the cells adhered thereto. Further, in order to investigate whether LM411E8 has a function to induce vascular endothelial differentiation by itself, the mesodermal progenitor cells on Day 3 after the induction of differentiation were cultured on LM411E8 without VEGF. As a result, no induction to vascular endothelial cells was observed. In other words, it has been revealed that LM411E8 itself does not have a function to induce vascular endothelial differentiation.

The above results suggest that LM411E8 plays an important role in the selection of progenitor cells and the determination of the direction of subsequent differentiation, in the VEGF-dependent vascular endothelial differentiation of mesodermal progenitor cells.

Single-Cell RNA-Sequencing

Figure 14:
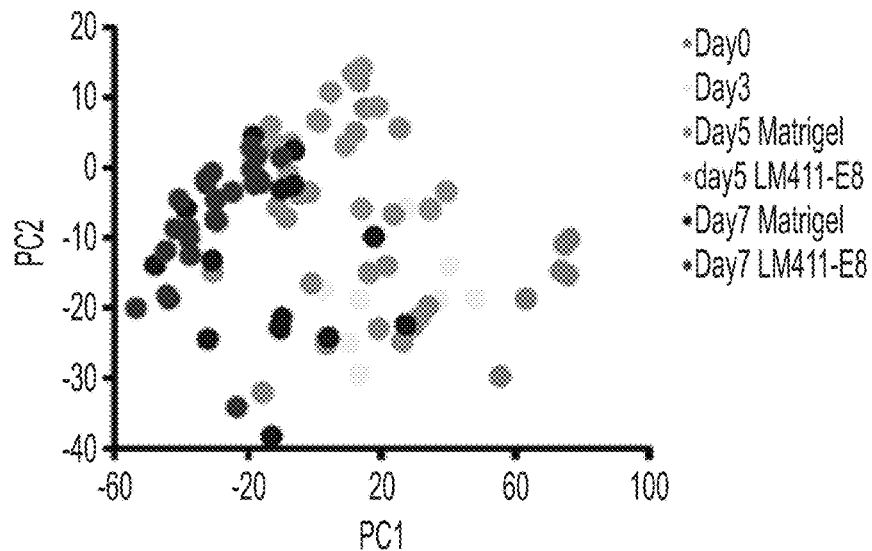
FIG. 14 shows the results of single-cell RNA-sequencing in pluripotent stem cells (Day 0), mesodermal progenitor cells (Day 3), and the cells differentiated on Matrigel or LM411E8 on Day 5 (Day 5 Matrigel or Day 5 LM411E8) and Day 7 (Day 7 Matrigel or Day 7 LM411E8).

Single-cell RNA-sequencing was carried out, in order to examine in detail how the selection of matrices affects the individual cells during the process of differentiation from mesodermal progenitor cells to vascular endothelial cells. When carrying out the sequencing, the mesodermal progenitor cells (Day 3) which had been differentiated from the pluripotent stem cells using BMP4/Matrigel were dissociated into single cells, and then differentiated on Matrigel or LM411E8. The gene expression was compared between the cells on Day 5 and Day 7 after the induction of differentiation at the single cell level (FIG. 14). A principal component analysis was performed to reveal that, although the gene expression varied relatively during the period of from Day 0 to Day 3 after the induction of differentiation, the cells re-seeded on LM411E8 formed a homogeneous population. On the other hand, the heterogeneity in the gene expression did not improve in the cells differentiated on Matrigel. The above results have demonstrated that LM411E8 functions as a guide to restrict the gene expression profile, in the determination of the destiny of the cells, also in terms of gene expression profile. Further, the vascular endothelial cells obtained by using LM411E8 or Matrigel, on Day 5 after the induction of differentiation, were subjected to a microarray analysis to perform Gene Set Enrichment Analysis (GSEA). The results suggest that the Rho family GTPase pathway is activated in the cells obtained by using LM411E8.

Example 2

Improvement in Differentiation Efficiency of Mesodermal Progenitor Cells by Wnt Signal Enhancement It is known that the activation of the Wnt/β-catenin signal results in an increase in the induction efficiency of mesodermal differentiation (Sumi, T., et al., Development. 135: pp. 2969 to 2979, 2008), and CHIR99021, which is a potent GSK3β inhibitor, is used for inducing the differentiation into hemocytes and endothelial cells (Sturgeon, C, et al., Nat Biotechnol. 32: pp. 554 to 561, 2014). The results of Single cell RNA-sequencing have shown that the increase in AXIN2, which is a known reporter gene for Wnt signaling, was not uniform at the single cell level in the cells on Day 3 after the induction of differentiation. This revealed that the endogenous activation of the Wnt/β-catenin pathway was not sufficient in the early differentiation. Based on the results of Single cell RNA-sequencing, it was thought that the use of a conventional method results in an uneven activation of endogenous Wnt signaling in the early differentiation, and accordingly, that it may be possible to increase the number of the cells which adhere to LM411E8 and thus differentiate into vascular endothelial cells, by uniformly activating the Wnt/β-catenin signaling by the use of CHIR99021. Further, it was also thought that it may be possible to successively enhance the differentiation from the mesodermal progenitor cells expressing KDR to vascular endothelial cells, by adding VEGF in the early stages of differentiation.

Figure 15:
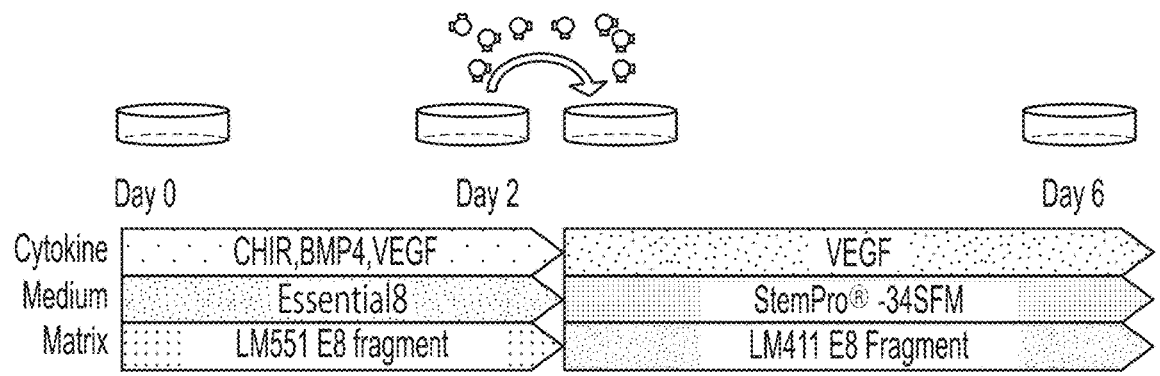
FIG. 15 shows a scheme for inducing the differentiation into vascular endothelial cells used in Example 2.

Therefore, the pluripotent stem cells were seeded on a plate coated with LM511E8 fragment at a density of 5 colonies/cm$^2$ and then cultured in mTeSR1 medium. The cells were allowed to grow until the diameters of the colonies were 750 μm, and then the medium was replaced with Essential 8 (Life Technologies) medium containing 4 μm CHIR99021 (Wako), 80 ng/mL of BMP4 and 80 ng/mL of VEGF, to initiate the induction of differentiation (FIG. 15). On day 2 after the start of the differentiation induction, the cells were dissociated into single cells by treating the cells with TrypLE Express at 37° C. for 20 minutes, and the resulting cells were suspended in Stempro-34 medium containing 80 ng/mL of VEGF, seeded on a plate coated with LM411E8 at a density of $4\times10^4$ cells/cm$^2$, and cultured for four days.

Figure 16:
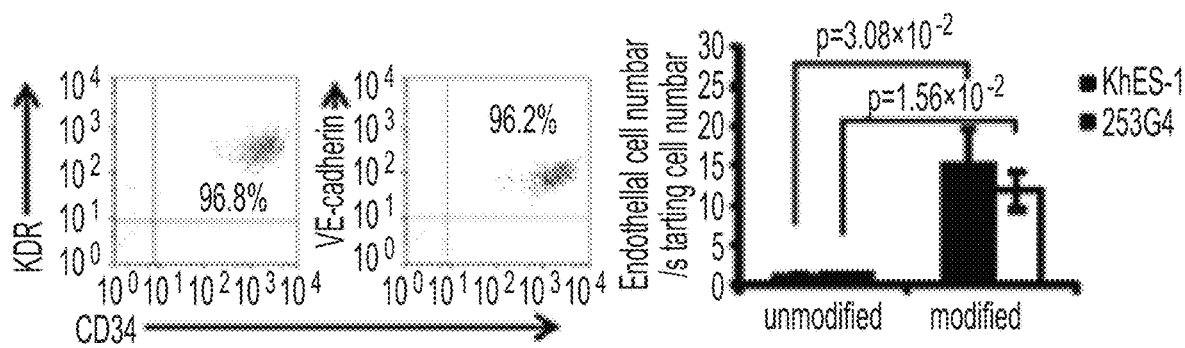
FIG. 16 shows: the results (halftone images) obtained by analyzing the expression of KDR, CD34 and VE-Cadherin by flow cytometry in the cells obtained by an improved differentiation induction method (left); and a graph illustrating the ratio of the number of vascular endothelial cells per initial cell count (right) in the cells induced under the conditions before the improvement (unmodified) or the conditions after the improvement (modified).
Figure 17:
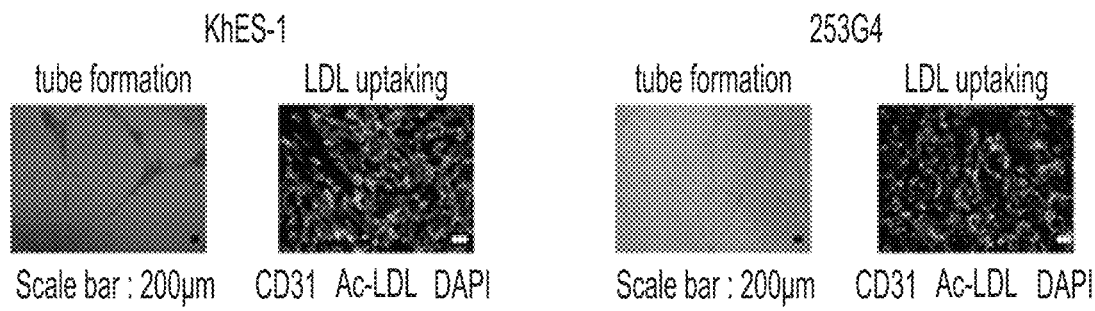
FIG. 17 shows photographs of: phase-contrast images (left) obtained by observing the tube formation of endothelial cells induced from ES cells (KhES-1) and iPS cells (253G4) by the improved differentiation induction method; and images (right) stained for CD31 (green), incorporated Ac-LDL (red) and DAPI (blue).

As a result, it has been shown that the mesodermal progenitor cells induced under the improved early differentiation conditions, as described above, are also compatible with the culture system in which LM411E8 was used as the second matrix, and that it is possible to induce vascular endothelial cells at a high purity (the images on the left in FIG. 16), and to induce ten or more vascular endothelial cells from one pluripotent stem cell (the graph on the right in FIG. 16). Further, these endothelial cells were also confirmed to have functions to form cord-like structures (tube formation) and to incorporate Ac-LDL (FIG. 17).

Angiogenic Capacity In Vivo

The induced vascular endothelial cells obtained as described above were suspended at a density of $1\times10^7$ cells/mL, in Matrigel supplemented with bFGF (Wako) to a concentration of 300 ng/mL. A quantity of 100 μL of the resulting suspension was injected subcutaneously to the back of an NOG mouse (around 6 week-old) (Nakahara M, et al, cloning and stem cells, 11: pp. 509 to 522, 2009). The Matrigel was taken on Day 21 after the transplantation, and analyzed by immunofluorescent staining. Specifically, the Matrigel was fixed with 4% paraformaldehyde (Wako) at 4° C. overnight. Subsequently, the paraformaldehyde was replaced with a 20% sucrose solution at 4° C. overnight, and frozen embedded using an O.C.T. compound. The resultant was cut into a section having a thickness of 6 μm, and the section was allowed to adsorb onto a glass slide. After drying, the section was fixed by treating with Cytofix at room temperature for five minutes. Thereafter, the section was incubated using Perm/Wash at room temperature for 30 minutes to enhance the permeability, and an antibody reaction was carried out. A sheep anti-CD31 antibody (BD Biosciences, 1:10), a mouse anti-human nuclear antibody (Millipore, 1:100), and a rat Alexa fluor 647-labeled anti-mouse TER-119 antibody (BD Biosciences, 1:10), as primary antibodies, were dissolved in Perm/Wash, and the reaction was allowed to proceed at room temperature for two hours. For the secondary antibody reaction, an anti-sheep IgG antibody (Jackson immunoresearch, 1:100) and an anti-mouse IgG antibody (Jackson immunoresearch, 1:100) were dissolved in Perm/Wash, and the reaction was allowed to proceed at room temperature for one hour. Images were captured using a fluorescence microscope (OLYMPUS, fluoview).

Figure 18:
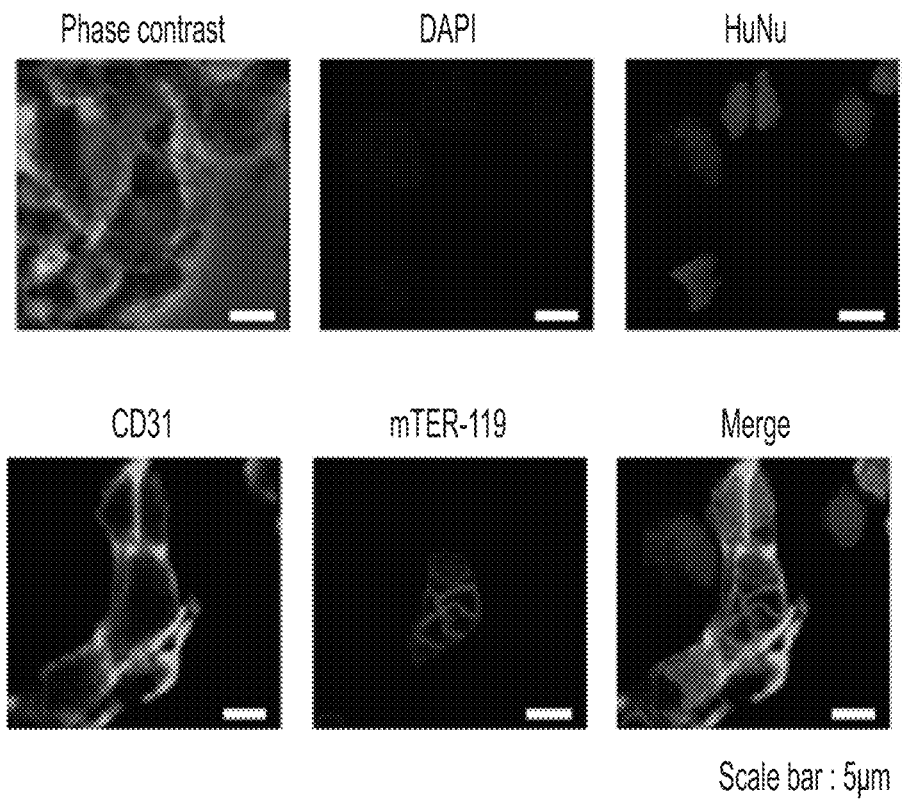
FIG. 18 shows photographs of phase-contrast images and fluorescent images (DAPI, HuNu, CD31 and mTER-119, and a combined image of these) of the sections collected on Day 21 after the transplantation of the induced vascular endothelial cells into an NOG mouse by subcutaneous injection.

As a result, it has been confirmed that the vascular endothelial cells induced by the present method have formed a luminal structure in vivo, and mouse erythrocytes are present in the lumens (FIG. 18). In other words, it has been shown that it is possible to induce functional vascular endothelial cells by the matrix switching method using LM411E8, also in vivo.

INDUSTRIAL APPLICABILITY

The present invention enables the production of vascular endothelial cells from pluripotent stem cells such as ES cells and iPS cells. The resulting vascular endothelial cells can be used in the field of revascularization medicine, aimed at treating patients with ischemic diseases including coronary artery disease and lower limb ischemic diseases (such as Buerger's disease, obstructive arteriosclerosis, etc.).

What is claimed is:

1. A method for producing vascular endothelial cells from pluripotent stem cells, the method comprising:
   (i) culturing pluripotent stem cells in a culture medium comprising a BMP, on a culture vessel coated with a first matrix, to produce mesodermal progenitor cells;
   (ii) dissociating the mesodermal progenitor cells obtained in the culturing of the pluripotent stem cells into single cells; and
   (iii) culturing the cells obtained by the dissociating of the mesodermal progenitor cells in a culture medium comprising VEGF, on a culture vessel coated with a second matrix selected from the group consisting of laminin-411 or a fragment thereof having an avidity for integrin, and, laminin-511 or a fragment thereof having an avidity for integrin.

2. The method according to claim 1, wherein the second matrix used in the culturing of the cells obtained by the dissociating of the mesodermal progenitor cells is a fragment of laminin-411 having an avidity for integrin.

3. The method according to claim 1, wherein the fragment of laminin-411 is laminin-411 E8.

4. The method according to claim 1, wherein the first matrix used in the culturing of the pluripotent stem cells is Matrigel, or laminin-511 or a fragment thereof having an avidity for integrin.

5. The method according to claim 4, wherein the fragment of laminin-511 used in culturing of the pluripotent stem cells is laminin-511 E8.

6. The method according to claim 1, wherein the BMP is BMP4.

7. The method according to claim 1, wherein the culture medium used in the culturing of the pluripotent stem cells further comprises a GSK3β inhibitor and VEGF.

8. The method according to claim 7, wherein the GSK3β inhibitor is CHIR99021.

9. The method according to claim 1, wherein the culturing of the pluripotent stem cells is carried out for two days or three days.

10. The method according to claim 1, wherein the culturing of the cells obtained by the dissociating of the mesodermal progenitor cells is carried out for four days.

* * * * *